(12) United States Patent
Denison et al.

(10) Patent No.: US 10,463,511 B2
(45) Date of Patent: Nov. 5, 2019

(54) STENT HAVING AT LEAST ONE CONNECTING MEMBER CONFIGURED TO CONTROLLABLY SEVER IN VIVO

(71) Applicant: CELONOVA STENT, INC., San Antonio, TX (US)

(72) Inventors: Andy Edward Denison, Temecula, CA (US); Mark C. Bates, Charleston, WV (US); Kent C. B. Stalker, San Marcos, CA (US)

(73) Assignee: CELONOVA STENT, INC., San Antonio, TX (US)

( * ) Notice: Subject to any disclaimer, the term of this patent is extended or adjusted under 35 U.S.C. 154(b) by 638 days.

(21) Appl. No.: 14/944,559

(22) Filed: Nov. 18, 2015

(65) Prior Publication Data

US 2016/0067068 A1    Mar. 10, 2016

Related U.S. Application Data

(62) Division of application No. 13/403,793, filed on Feb. 23, 2012, now Pat. No. 9,220,615.

(Continued)

(51) Int. Cl.
*A61F 2/89* (2013.01)
*A61F 2/88* (2006.01)
(Continued)

(52) U.S. Cl.
CPC .............. *A61F 2/89* (2013.01); *A61F 2/88* (2013.01); *A61F 2/915* (2013.01);
(Continued)

(58) Field of Classification Search
CPC .... A61F 2/89; A61F 2/915; A61F 2/88; A61F 2250/0071; A61F 2002/91591; A61F 2002/91575; A61F 2/82
See application file for complete search history.

(56) References Cited

U.S. PATENT DOCUMENTS

| | | |
|---|---|---|
| 6,488,702 B1 | 12/2002 | Besselink |
| 2002/0111671 A1* | 8/2002 | Stenzel ..................... A61F 2/91 623/1.16 |

(Continued)

FOREIGN PATENT DOCUMENTS

| | | |
|---|---|---|
| EP | 1782766 A2 | 5/2007 |
| EP | 1985262 A2 | 10/2008 |

(Continued)

OTHER PUBLICATIONS

"The extended European search report", European Patent Application No. 13751579.7, European Patent Office, dated Nov. 27, 2015, 7 pages.

(Continued)

*Primary Examiner* — Ashley L Fishback
(74) *Attorney, Agent, or Firm* — Mannava & Kang, P.C.; Carol L. Bunner

(57) ABSTRACT

A stent may include a connector having a first portion, a second portion, and a third portion positioned between the first and second portions. The connector may be configured to interconnect axially adjacent stent segments. The connector may be further configured such that the third portion severs in response to a threshold amount of axial force, axial foreshortening, and/or cyclic loading or fatigue, in order to predispose the severance of one or more pre-configured connectors in a controlled manner to minimize any potential harm to the surrounding vasculature of a patient.

17 Claims, 28 Drawing Sheets

Related U.S. Application Data

(60) Provisional application No. 61/446,031, filed on Feb. 23, 2011.

(51) Int. Cl.
*A61F 2/915* (2013.01)
*A61F 2/82* (2013.01)

(52) U.S. Cl.
CPC .............. *A61F 2002/828* (2013.01); *A61F 2002/91575* (2013.01); *A61F 2002/91591* (2013.01); *A61F 2250/0071* (2013.01)

(56) References Cited

U.S. PATENT DOCUMENTS

| | | |
|---|---|---|
| 2003/0078649 A1 | 4/2003 | Camrud et al. |
| 2003/0135266 A1 | 7/2003 | Chew et al. |
| 2006/0069424 A1 | 3/2006 | Acosta et al. |
| 2006/0155360 A1 | 7/2006 | Calisse et al. |
| 2007/0213810 A1* | 9/2007 | Newhauser ............... A61F 2/91 623/1.16 |
| 2007/0219612 A1 | 9/2007 | Andreas et al. |
| 2008/0097576 A1 | 4/2008 | Cottone et al. |
| 2008/0269872 A1 | 10/2008 | Lootz et al. |
| 2008/0319528 A1 | 12/2008 | Yribarren et al. |
| 2009/0036970 A1* | 2/2009 | Ma ............................ A61F 2/91 623/1.15 |
| 2009/0210049 A1 | 8/2009 | Thielen et al. |
| 2009/0228088 A1 | 9/2009 | Lowe et al. |
| 2010/0324657 A1 | 12/2010 | Bogert |
| 2011/0066225 A1 | 3/2011 | Trollsas et al. |
| 2011/0224777 A1* | 9/2011 | Von Oepen ............... A61F 2/91 623/1.16 |

FOREIGN PATENT DOCUMENTS

| | | |
|---|---|---|
| JP | 2007125394 | 5/2007 |
| JP | 2008119490 | 5/2008 |
| JP | 2008514297 | 5/2008 |
| JP | 2009-178228 | 8/2009 |
| JP | 2009178228 | 8/2009 |
| JP | 2009530060 | 8/2009 |
| WO | 2011/032526 A1 | 3/2011 |

OTHER PUBLICATIONS

PCT/US2013/027330 International Search Report and Written Opinion dated Apr. 19, 2013.

* cited by examiner

STENT HAVING AT LEAST ONE CONNECTING MEMBER CONFIGURED TO CONTROLLABLY SEVER IN VIVO

CROSS-REFERENCE TO RELATED APPLICATION

This application is a divisional of U.S. application Ser. No. 13/403,793, filed on Feb. 23, 2012, now allowed, which claims priority to U.S. Provisional Patent Application No. 61/446,031, filed Feb. 23, 2011, both of which are hereby incorporated by reference in their entirety.

INCORPORATION BY REFERENCE

U.S. Pat. No. 6,488,702, filed on Jan. 23, 1998, entitled BISTABLE SPRING CONSTRUCTION FOR A STENT AND OTHER MEDICAL APPARATUS, U.S. patent application Ser. No. 11/875,718, filed on Sep. 19, 2007, entitled DEFORMABLE LUMEN SUPPORT DEVICES AND METHODS OF USE, and U.S. patent application Ser. No. 11/391,940, filed on Mar. 29, 2006, entitled "FRACTURE-RESISTANT HELICAL STENT INCORPORATING BISTABLE CELLS AND METHODS OF USE," which are attached hereto as Exhibit A, are hereby incorporated by reference in their entireties as if fully set forth herein.

BACKGROUND OF THE DISCLOSURE

Technical Field

The present disclosure relates to stents, more particularly, to interconnections, connectors, and interconnects between adjacent, e.g. axially adjacent, stent segments.

It is known by persons skilled in the art that a stent positioned in blood vessels adjacent joints or bending planes of the body, such as a superficial femoral artery (SFA), can experience repeated and extreme axial loads or displacements in use. For this reason, some embodiments of the stents positioned within the SFA or other such locations preferably are axially resilient or springy, as opposed to being axially rigid. In some cases, coiled stents have been used in these locations, but such stents often do not deploy well or cover the vessel or passage wall well. It may be desirable to provide stents having improved performance in this environment.

SUMMARY OF SOME EXEMPLIFYING EMBODIMENTS

In one embodiment, a stent is provided that comprises a connector. The connector includes a first portion, a second portion, and a third portion positioned between the first and second portions. The connector is configured to interconnect axially or longitudinally adjacent stent segments. The connector is configured such that the third portion thereof severs in a controlled manner during or after deployment.

For example, the stent can be configured to induce sufficient stress in the third portion under the forces that arise within a vessel that is compressed due to bending of the human anatomy, e.g., at a bending plane. As such, the third portion can be configured to sever at a predetermined axial force, which may be applied by the vasculature along the length of the stent.

In some embodiments, the third portion is configured to sever when under a predetermined percent of axial foreshortening, such as once the stent has been shortened by approximately 3% percent or more due to an applied load.

In some embodiments, the third portion can be configured to sever upon exceeding a predetermined number of cycles of loading such that the stent comprises a unitary body from proximal to distal end for at least an initial period after deployment and thereafter separates into a plurality of adjacent scaffolding segments after the initial period.

In another embodiment, an expandable device is provided that includes at least first and second cells that are connected by a load absorbing member. The load absorbing member can be configured to accommodate for an axial load placed on the expandable device such that the expandable member can scaffold, e.g., hold open, a passage or lumen, and can at the same time accommodate axial contraction of the passage or lumen.

The load absorbing member can be configured as a breakable member that enables the expandable member to be delivered in a unitary state and thereafter separate into at least two separate structures during or after deployment. In some embodiments, one or more connecting members of an expandable device break and one or more connecting members of the expandable device remain intact. For example, where bending is primary mode of deformation of the expandable device, not all members necessarily break. In some embodiments, breakable members that are subject to largest strains in bending break to create higher flexibility for bending while other members can remain intact. As a result the flexibility of the stent can be enhanced during or after delivery while the stent does not separate into two or more separate structures.

In one arrangement, a breakable member can comprise a first portion coupled with the first cell and a second portion coupled with the second cell. The breakable member can be configured to fracture between the first and second cells in a controlled manner. For example, the breakable member can be configured to fracture under a pre-determined axial load. The breakable member can be configured to fracture under a number of axial compression cycles. The breakable member can be configured to fracture upon expansion.

In some applications, further advantage is provided by shielding surfaces that are exposed due to fracture of a breakable member. Shielding surfaces exposed due to fracture can be accomplished by providing atraumatic structures on at least two sides of the fracture-exposed surface. For example, the connector can comprise first and second portions that extend between the breakable member and cells of the expandable member, where the first and second portions are configured to shield the fracture-exposed surfaces.

In some techniques, fracture-exposed surfaces can be oriented or can be configured to face in a direction expected to have the least movement or contraction during cycles. For example, in the superficial femoral artery, greater foreshortening is expected along the length of the vessel than about the circumference. Thus, there may be advantage in orienting the fracture-exposed surface generally circumferentially in such applications.

In some embodiments, the breakable portion extends directly between cells of the expandable device and the cells are constructed to shield fracture-exposed surfaces.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF SOME EXEMPLIFYING EMBODIMENTS

Figure 1:
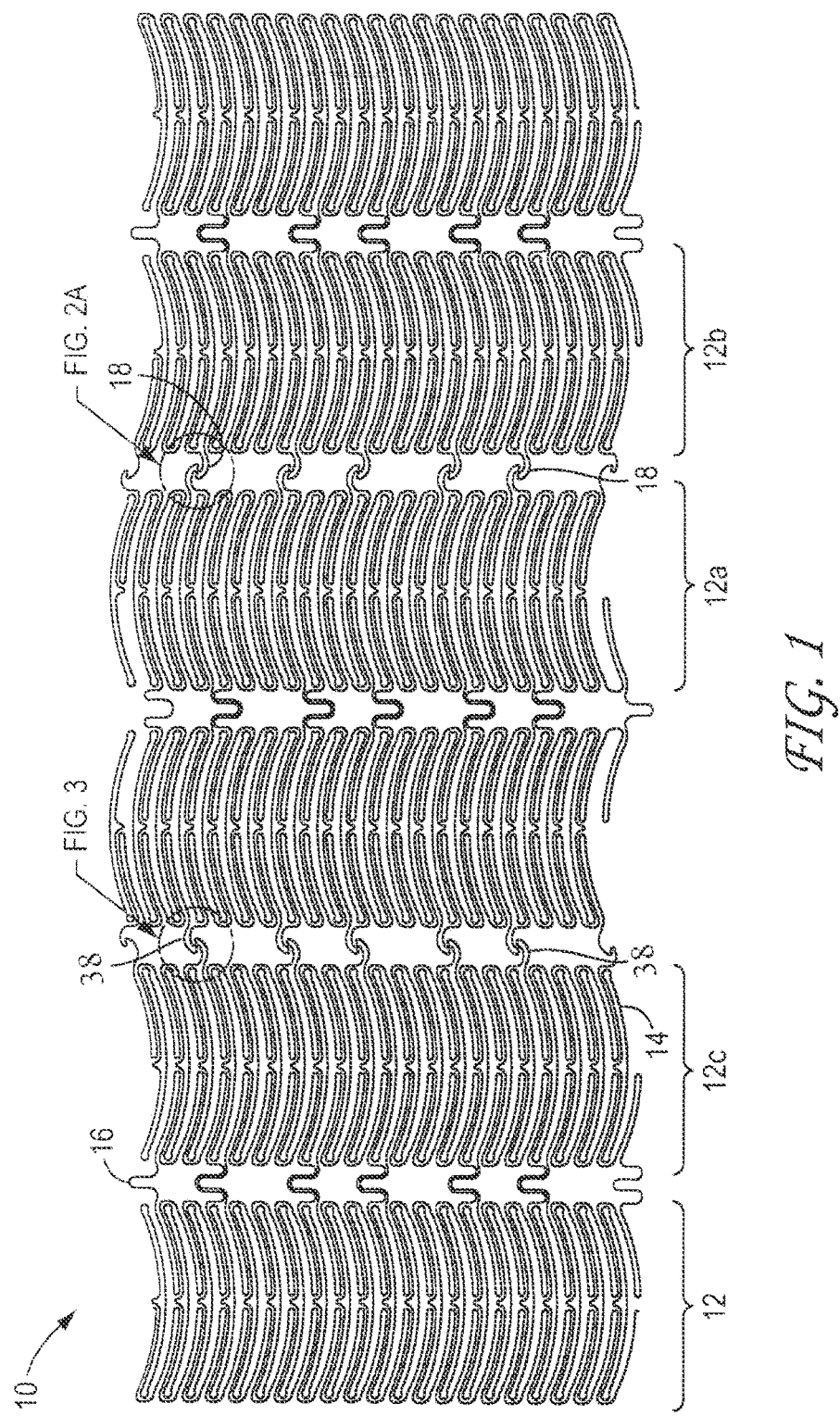
FIG. 1 is a plan view of a pattern of an embodiment of a stent.

The following detailed description is now directed to certain specific embodiments of the disclosure. In this description, reference is made to the drawings wherein like parts are designated with like numerals throughout the description and the drawings.

Certain embodiments described herein are directed to systems, methods, and apparatuses to treat stenosis, lesions, or other defects in tubular structures like blood vessels, including, but not limited to, the aorta, iliac arteries or veins, coronary arteries, femoral arteries, thoracic arteries, and/or the superficial femoral artery, to name a few. However, the systems, methods, and apparatuses may have application to other vessels or areas of the body such as biliary vessels or ducts, or to other fields, and such additional applications are intended to form a part of this disclosure. And, while specific embodiments may be described herein with regard to particular portions of a person's vasculature, it is to be understood that the embodiments described can be adapted for use in other portions of a person's or animal's vasculature or other portions of the body and are not limited to the specific blood vessels specified herein.

A stent positioned in blood vessels adjacent joints or bending planes of the body, such as a superficial femoral artery, can experience repeated and extreme axial loads or displacements in use. For this reason, some embodiments of the stents positioned within the SFA or other such locations preferably are axially resilient or springy, as opposed to being axially rigid. In some cases, coiled stents have been used in these locations, but such stents often do not deploy well or cover the vessel or passage wall well. Generally, without limitation, some stent embodiments disclosed herein provide improved performance in this environment, for example providing a controlled deployment thereof. In some embodiments, stents are provided with severable or breakable connectors (also referred to herein as interconnectors) that are designed to sever or break when the stent experiences a threshold or predetermined displacement, a threshold force, or when the stent experiences a threshold or predetermined level of cyclic loading or fatigue. The calculated metal fatigue yield threshold will depend in part on the target vessel domain or clinical indication. For example, Dr. Smouse et. al (Endovascular Today (1) June 2005) showed in a human cadaver study that the bare SFA shortens between 5 and 23% and a stent implanted in the SFA shortens on average between 4 and 14% with knee flexion. Thus for the SFA it may be best to have a device yield at a degree of foreshortening at or below these percentages, for example some embodiments have connectors that break at or less than 3% foreshortening. The levels of foreshortening at which the connectors break may be much lower in venous and coronary vessels and much higher in hemodialysis outflow stenosis as examples. The target foreshortening range after severing inter-connects will be between 2% and 25% for most applications.

In some cases, it is desirable to configure the interconnect to break or sever at or above a level of force. For example, in some applications 0.8 pounds or less force can result in breaking of an interconnect in an SFA application.

For example, without limitation, some embodiments of the stents disclosed herein can be configured such that one or more axial connectors sever or separate when the stent experiences an axial foreshortening of approximately 2% or more. In some cases, a higher threshold of foreshortening may be appropriate. For example, interconnects can be configured to disengage after a number of cycles of shortening that exceed 3%. In some applications, interconnects can be arranged that disengage after a number of cycles of more than about 5% foreshortening occur. Some interconnect can be arranged to not disengage until a number of cycles of shortening greater than 10% occur and in some cases as much as 20%. The threshold for stent foreshortening to cause fracture will be much less than the expected need for overall stent foreshortening in most embodiments. The distance between the circumferential structures or rings after release or disengagement of interconnects can be designed based on the intended anatomy. The overall stent axial compressibility for the SFA applications as an example would be between 5 and 25%.

After one or more connectors have become severed or portions of adjacent stent segments have become disengaged, the stent can be more flexible in at least the axial direction to better accommodate the foreshortening or stretching of the vessel or passageway that the stent is positioned within. Additionally, in some embodiments, delivery and deployment of a stent with unsevered connectors may be easier and safer for the patient. In some cases, segments along the length of the stent can be completely separated from each other due to severing of one or more connectors.

Accordingly, some embodiments of the stents disclosed herein can be configured to compress or foreshorten by approximately 25%, or between approximately 10% and approximately 40%. Some embodiments of the stents disclosed herein can be configured to compress or foreshorten between approximately 10% and approximately 20%, or between approximately 20% and approximately 30%, or between approximately 30% and approximately 40% of its axially uncompressed length, or to or from any values within these ranges.

In some embodiments, the connectors between axial segments can be configured so as to sever or separate at a threshold force at a predetermined location of the connector. For example, without limitation, a portion of a connector can have a reduced cross-sectional area or thickness and can be otherwise configured so as to sever or separate when the stent experiences a predetermined axial force or foreshortening.

Additionally, in some embodiments, the connectors between axial segments can be configured so as to sever or separate at a predetermined location of the connector when a threshold force is imparted on the stent or connector. For example, without limitation, a portion of a connector can have a reduced cross-sectional area and can be otherwise configured so as to sever or separate when the stent experiences a predetermined axial force or foreshortening, or after the stent or connector has undergone a predetermined level of cyclic loading or fatigue.

Additionally, in some embodiments, the connectors can be formed of the same material as the cells of the stent, or can be partially or substantially completely formed from a bioabsorbable or biodegradable material that is configured to degrade or be bioabsorbed by the body after a predetermined period of time. In this configuration, the connector can be weakened so as to be more easily severable after a predetermined period of time, or can be completely bioabsorbed so as to remove the connection between adjacent stent segments after a predetermined period of time.

FIG. 1 shows a plan view of a pattern of an embodiment of a stent 10 having a plurality of stent segments 12 comprising a plurality of stent cells 14. In some embodiments, the stent cells 14 of each stent segment 12 can be interconnected in a circumferential direction. In use, the stent 10 can define a generally straight or curved cylindrical or tubular shape. The stent cells 14 or any other cells disclosed herein can be, but are not required to be, bistable cells, multistable cells, deformable unit cells, open cells, or other cells of the types disclosed in U.S. Pat. No. 6,488,702, filed on Jan. 23, 1998, entitled BISTABLE SPRING CONSTRUCTION FOR A STENT AND OTHER MEDICAL APPARATUS, or U.S. patent application Ser. No. 11/875,718, filed on Sep. 19, 2007, entitled DEFORMABLE LUMEN SUPPORT DEVICES AND METHODS OF USE, both of which are hereby incorporated by reference as if fully set forth herein. In some embodiments, the stent cells 14 or any other cells disclosed or incorporated by reference herein can be similar to those of any expandable stents currently known or later developed, including without limitation self-expandable cells, and balloon or other mechanically expandable cells or any combination of any of the foregoing. Further, in some embodiments, the stent segments 12 can have an open stent pattern (serpentine or otherwise) comprising a series of concave and convex bends, or any other suitable structure.

In some embodiments, one or more adjacent stent segments 12 can be interconnected by one or more, or by any combination of, curved or straight connectors such as, without limitation, curved connector 16 (which can be generally configured to withstand breakage during axial loading in normal operating conditions), while other adjacent stent segments 12 can be interconnected by one or more severable connectors 18. In some embodiments, all of the adjacent stent segments 12 can be interconnected by one or more severable connectors 18.

Figure 2A:
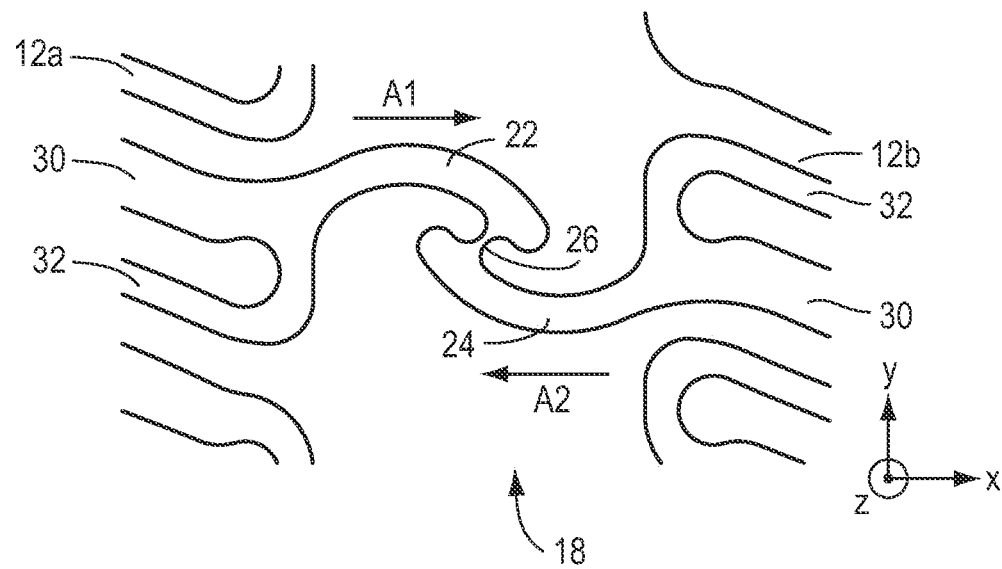
FIG. 2A is an enlarged view of a portion of the stent pattern shown in FIG. 1, defined by curve 2-2 of FIG. 1, showing the connector before a portion thereof has been severed.

FIG. 2A is an enlarged view of a portion of the stent pattern shown in FIG. 1, defined by curve 2-2 of FIG. 1. In particular, FIG. 2A is an enlarged view of the embodiment of the severable connector 18 shown in FIG. 1, the connector 18 being positioned between stent segment 12a and stent segment 12b. With reference to FIG. 2A, the severable connector 18 can comprise a first portion 22, a second portion 24, and a severable or third portion 26. The third portion 26 can be configured to become severed when the stent 10 experiences a threshold axial force or axial foreshortening, as described above.

In some embodiments, the third portion 26 can have a reduced cross-sectional area as compared to the first and second portions 22, 24 of the connector 18. In some embodiments, with reference to FIG. 2A, the thickness of the third portion 26 of the connector 18 can be reduced in either or both of the x and y directions. In some embodiments, the thickness of the third portion 26 of the connector 18 can be reduced in any or all of the x, y, and z directions, wherein the x-direction is parallel with the longitudinal axis of the stent, the y-direction is perpendicular to the longitudinal axis of the stent, and the z-direction is in perpendicular to both the x and y-directions (e.g., the radial direction relative to the stent).

In some embodiments, the cross-sectional area of the third portion 26 of the connector 18 can be approximately 50% less than a cross-sectional area of either or both of the first and second portions 22, 24 of the connector 18. Some embodiments of the connector 18 can be configured such that the third portion 26 of the connector 18 can have a cross-sectional area that is from approximately 20% to approximately 70% less than a cross-sectional area of either or both of the first and second portions 22, 24 of the connector 18, or from approximately 30% to approximately 50% less than a cross-sectional area of either or both of the first and second portions 22, 24 of the connector 18, or to or from any values within these ranges.

The connector 18 can be configured such that the third portion 26 undergoes a shear failure when a predetermined axial force or foreshortening is reached. For example, without limitation, the connector 18 can be configured such that the third portion 26 of the connector 18 experiences a significantly greater magnitude of shear strain than either of the first or second portions 22, 24 when the stent is axially foreshortened or compressed, or axially lengthened or stretched, or when torsional forces are imparted on the stent. With reference to FIG. 2A, arrows A1 and A2 represent directional vectors of a force that may be imparted on the connector 18 by stent segment 12a and stent segment 12b, respectively, when the stent 10 is compressed or axially foreshortened. As illustrated, the third portion 26 can be configured such that the cross-sectional area of the third portion 26 in a direction parallel to the force vectors A1 and A2 is less than the cross-sectional area of either of the first or second portions 22, 24 in a direction parallel to the force vectors A1 and A2 such that the third portion 26 fails in shear before either of the first or second portions 22, 24 fail. As such, the reduction of cross-section is one example of where the connector 18 is specifically configured to shear or break at a particular location. Other techniques can be used to configure a particular portion of the connector 18 to break such that partial or complete separation of adjacent circumferential portions of the stent 10 results. As a result the stent 10 is configured to provide adequate scaffolding and a sufficient prevention of prolapse of the vessel while at the same time enhancing flexibility to accommodate the repeated lengthening and shortening associated with an anatomical bending plane.

Figure 2B:
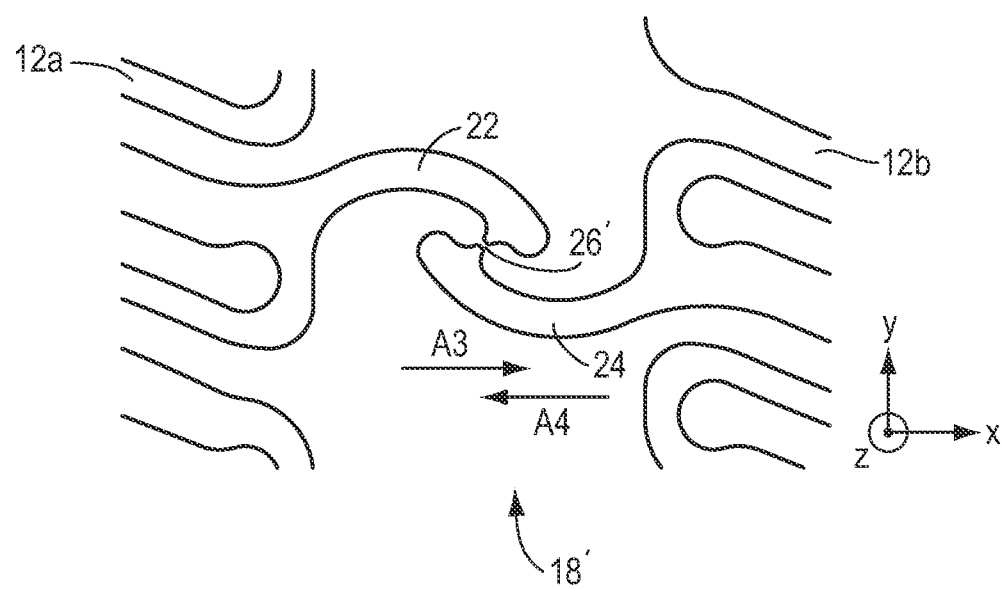
FIG. 2B is an enlarged view of a portion of the stent pattern shown in FIG. 1, defined by curve 2-2 of FIG. 1, showing the connector after a portion thereof has been severed.

FIG. 2B is an enlarged view of a portion of the stent 10 pattern shown in FIG. 1, defined by curve 2-2 of FIG. 1, showing a schematic illustration of the connector 18' after the third portion 26' thereof has been severed in response to an axial foreshortening of the stent 10, an axial force exerted on the stent 10, or a number of cycles of compression and tension applied thereto, and associated strain. As illustrated in FIG. 2B, after all of the connectors 18' interconnecting stent segments 12a, 12b have severed, the stent segments 12a, 12b can then be free to axially translate in the axial directions represented by arrows A3 and A4 relative to one another.

Further, with reference to FIGS. 1-2B, the first and second portions 22, 24 of the connectors 18 can be configured to partially or fully surround the third portion 26 of the connector 18 such that, after becoming severed, the potentially rough or jagged edges of the severed third portion 26' are shielded from the anatomy or other portions of the stent. The third portion can be shielded by being partially or fully surrounded in the x and y, or the axial, radial, and/or circumferential directions, thereby reducing the level of exposure of the severed connector. This configuration can prevent or reduce direct contact from the severed third portion 26' with other portions of the stent or adjacent body tissue. Additionally, as discussed above, the thickness of the third portion 26 can be reduced in a radial direction, for example, in the z-direction of the connector 18 shown in FIG. 2B, to further shield a patient's vasculature or other tissue from the potentially rough or jagged edges of the severed third portion 26'.

In some embodiments, as in the embodiment illustrated in FIGS. 1-2B, the cells 14 can each comprise a thick strut 30 and a thin strut 32 in communication with the thick strut 30. In this configuration, the connector 18 can be supported by the thick strut 30 of each of the adjacent cells 14 of the adjacent stent segments 12a, 12b. However, in other embodiments, the connector 18 can be supported by the thin strut 32 of either or both of the adjacent cells 14 of the adjacent stent segments 12a, 12b. Further, the connector 38 can be used to interconnect any desired portion of adjacent stent segments (having an open or closed cell structure, open serpentine pattern, or otherwise) and are, thus, not limited to interconnecting bistable stent cells as illustrated in some of the figures.

Figure 3:
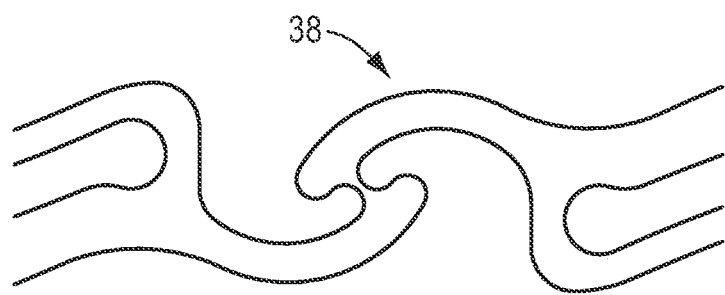
FIG. 3 is photograph of a connector, such as the connector defined by curve 3-3 of FIG. 1.

FIG. 3 is photograph of an embodiment of a connector 38, such as the connector 38 defined by curve 3-3 of FIG. 1. As shown in FIG. 3, the orientation of the connector 38 can be reversed as compared to the orientation of the connector 18. This can be due to the differing orientation of the cells 14 in the stent segment 14c as compared to the cells 14 of the stent segment 14a.

Figure 4A:
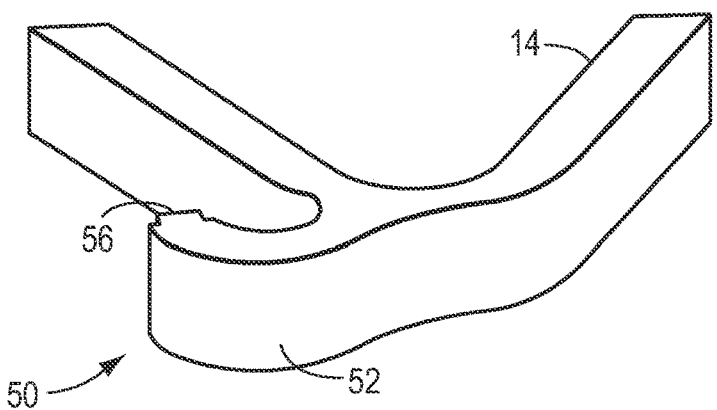
FIG. 4A is a perspective view of a portion of another embodiment of a connector and stent cell after a portion of the connector has been severed.
Figure 4B:
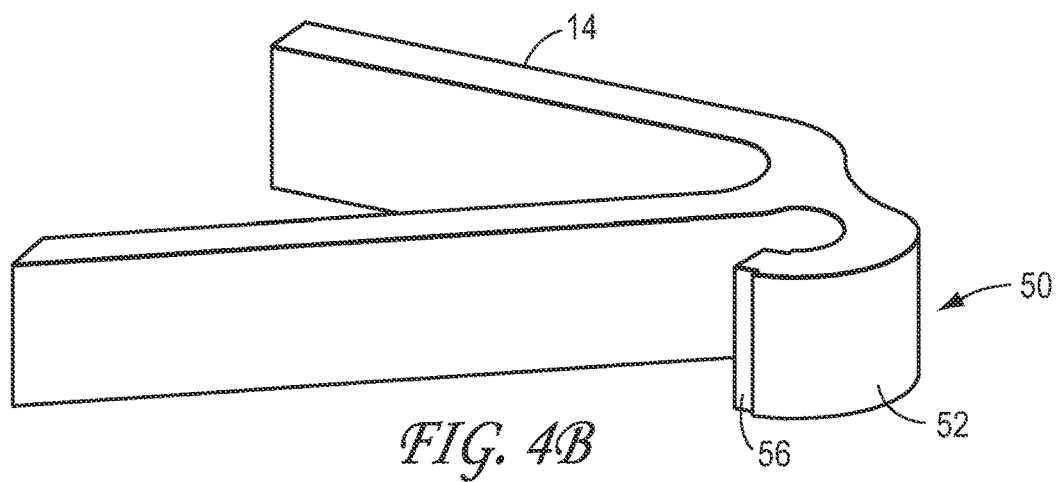
FIG. 4B is another perspective view of the embodiment of the connector and stent cell illustrated in FIG. 4A after a portion of the connector has been severed.
Figure 4C:
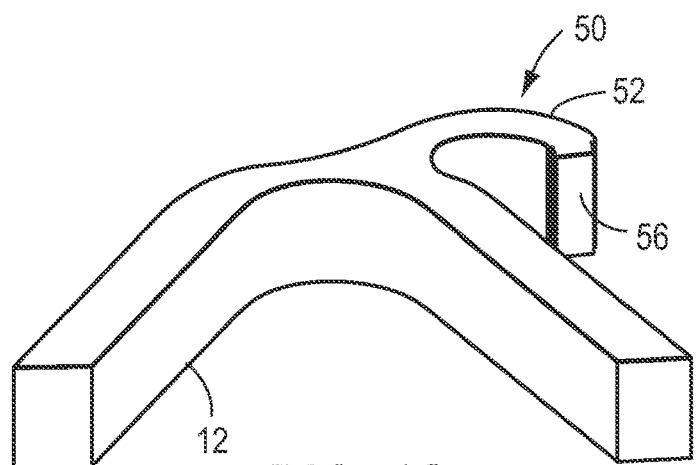
FIG. 4C is another perspective view of the embodiment of the connector and stent cell illustrated in FIG. 4A after a portion of the connector has been severed.

FIGS. 4A-4C are perspective views of a portion of another embodiment of a connector 50 and stent cell 12 after a portion of the connector 50 has been severed. The connector 50 can be used to interconnect any desired portion of adjacent stent segments (having an open or closed cell structure, open serpentine pattern, or otherwise) and are, thus, not limited to interconnecting bistable stent cells as illustrated in some of the figures.

With reference to FIGS. 4A-4C, the first portion 52 and a second portion (not illustrated) of the connector 50 can be configured to fully surround a severable or third portion 56 of the connector 50 such that, after becoming severed, the potentially rough or jagged edges of the severed third portion 56 are shielded from the anatomy or adjacent portions of the stent (which can be a covered or uncovered stent). The third portion can be shielded by being partially or fully surrounded in the axial, radial, and/or circumferential directions (similar to connector 18 described above). This arrangement is one way to reduce the level of exposure of the severed connector 50, e.g., to reduce the interaction between a vessel wall and the third portion 56. In some embodiments, it is sufficient that at least one of the first portion 52 and a second portion (not shown in FIGS. 4A-4C) partially surround or shield the third portion 56. This configuration can prevent or reduce direct contact from the severed third portion 56 with other portions of the stent or adjacent body tissue. Additionally, the thickness of the third portion 56 can be reduced in a radial direction to further shield a patient's vasculature or other tissue from the potentially rough or jagged edges of the severed third portion 56. In this context, the "radial direction" is the direction generally perpendicularly away from a central longitudinal axis of the passage defined through the stent.

Figure 5A:
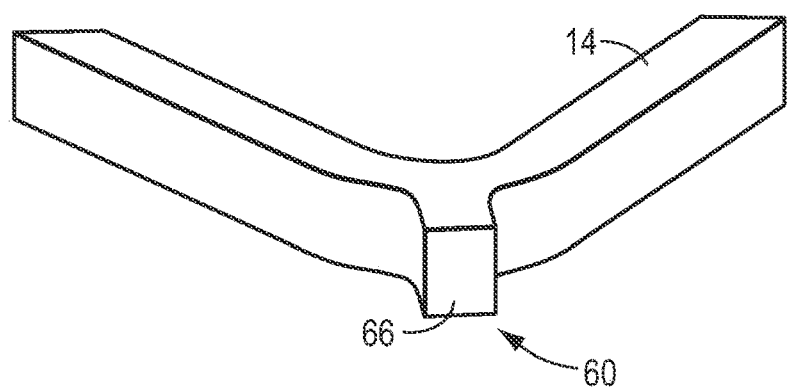
FIG. 5A is a perspective view of a portion of an embodiment of a breakable connector after a portion of the connector has been severed.
Figure 5B:
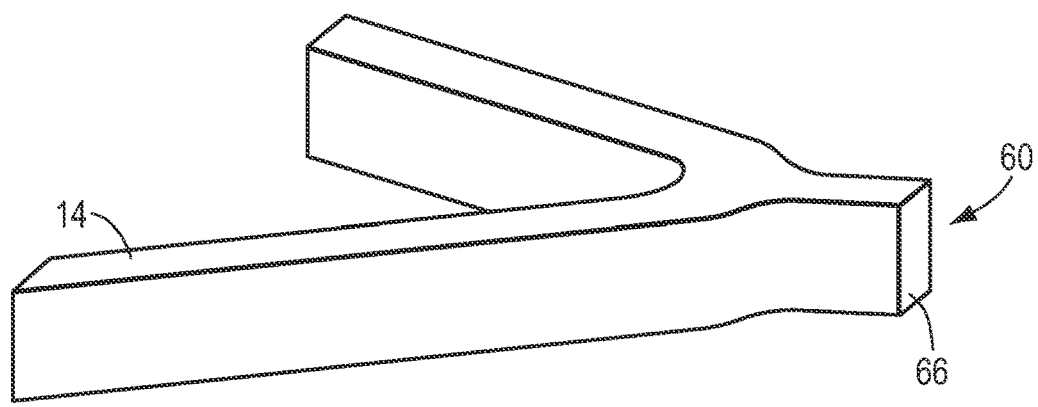
FIG. 5B is another perspective view of the embodiment of the breakable connector illustrated in FIG. 5A after a portion of the connector has been severed.
Figure 5C:
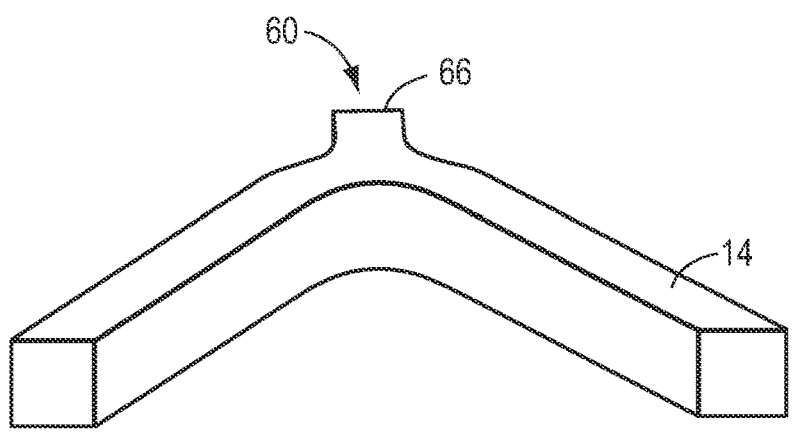
FIG. 5C is another perspective view of the connector illustrated in FIG. 5A after a portion of the connector has been severed.
Figure 5D:
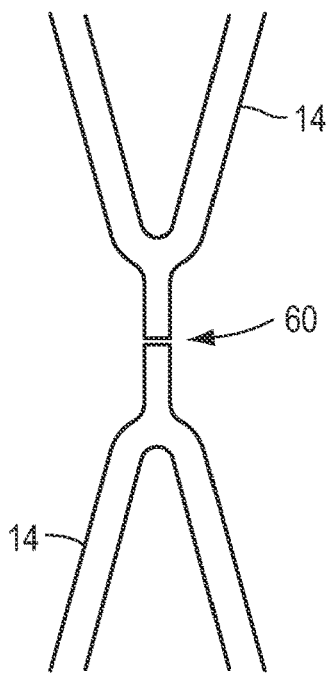
FIG. 5D is a plan view of another embodiment of a connector after the connector has been severed.
Figure 5E:
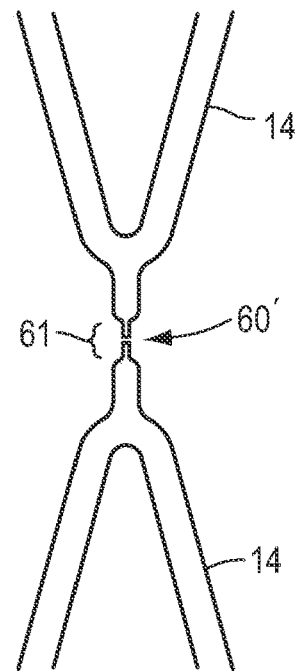
FIG. 5E is a plan view of another embodiment of a connector after the connector has been severed.
Figure 5F:
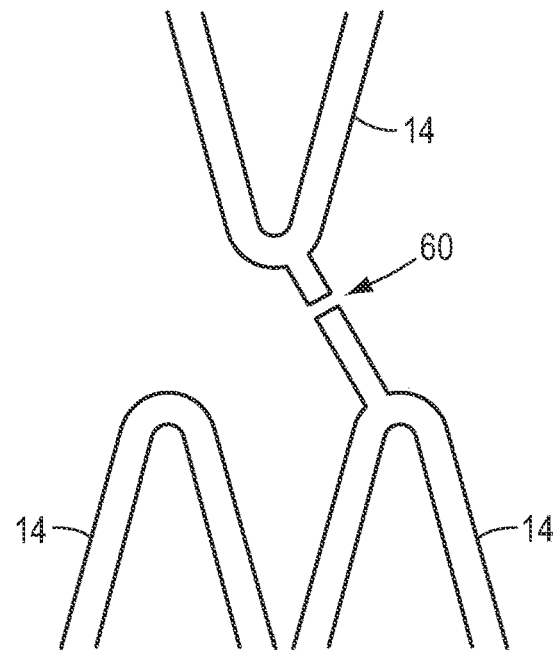
FIG. 5F is a plan view of another embodiment of a connector after the connector has been severed.

FIGS. 5A-5C are perspective views of a portion of a generally un-shielded severed connector 60, and FIGS. 5D-5F are plan view of other connectors after a portion of each connector has been severed. In contrast with other embodiments shown herein, such as connector 50, the connectors 60, 60' shown in FIGS. 5A-5F are not configured to partially or fully surround the severed portion or end of the connectors after the connectors have severed and are not atraumatic when artery undergoes bending or axial compression. As such, these connectors would be suited for vessels that do not experience bending or foreshortening or are otherwise unlikely to move relative to the severed ends. If such designs were deployed in the SFA or other vessel subject to bending, the end portion could cause damage to the vessel or irritation tending to produce restenosis. Thus, the embodiments with pockets and those that are shielded are more advantageous for the SFA and other similar vessels.

FIG. 5E illustrates one technique for controlling the separation of two longitudinally offset segments of a stent. The connector 60' can be formed with a portion that is configured to break in a controlled fashion. The connector 60' can be configured to concentrate stress at a pre-selected location so that a strain yield point can be reached at forces that are encountered in use. For example, the connector 60' can be configured to produce sufficient stress to be plastically deformed and in some cases rupture when subjected to forces generated in an SFA when the knee bends or has reached a predetermined number of strain cycles. Other similar forces generated at bending planes of the body could be the basis for defining a configuration of the connector 60'. In the embodiment of FIG. 5E, the connector has a portion 61 that has reduced cross-section compared to other portions of the connector 60'.

Figure 6:
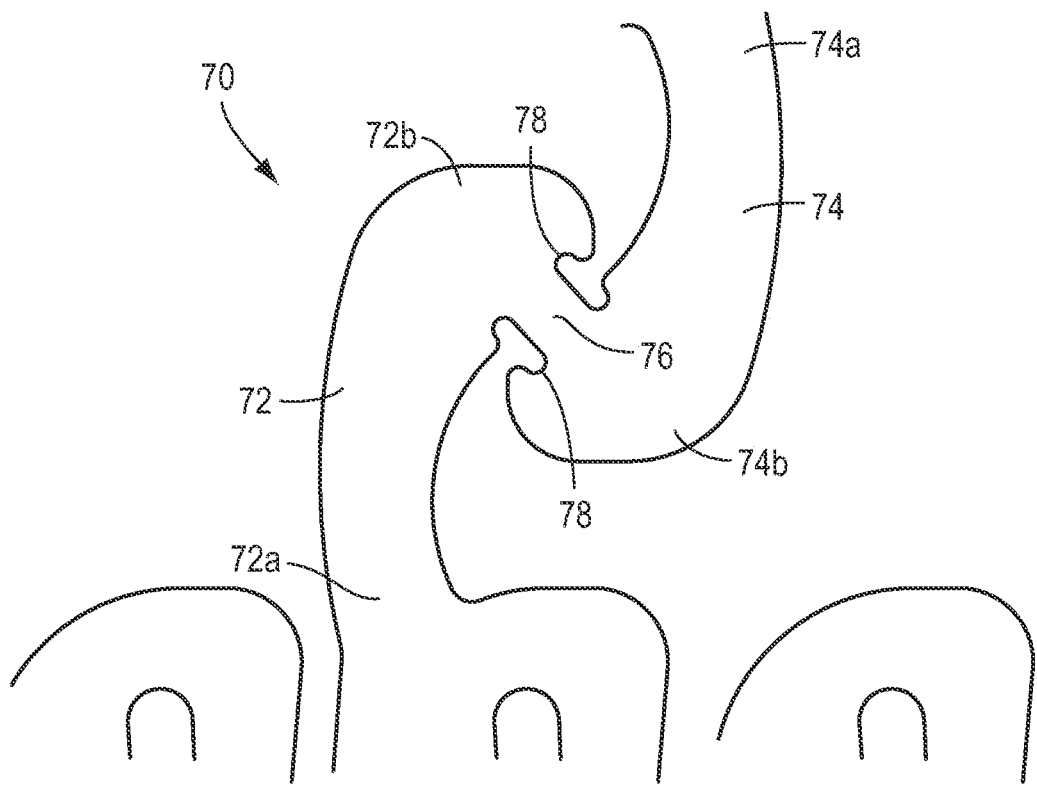
FIG. 6 is an enlarged plan view of another embodiment of a connector.

FIG. 6 is an enlarged plan view of another embodiment of a connector 70. The connector 70 can be used to interconnect any desired portion of adjacent stent segments (having an open or closed cell structure, open serpentine pattern, or otherwise) and are, thus, not limited to interconnecting bistable stent cells as illustrated in some of the figures.

With reference to FIG. 6, the first and second portions 72, 74 of the connector 70 can be configured to partially or fully surround a severable or third portion 76 of the connector 70 such that, after becoming severed, the potentially rough or jagged edges of the severed third portion 76 are shielded from the anatomy or adjacent portions of the stent. The third portion can be shielded by being partially or fully surrounded in the axial, radial, and/or circumferential directions (similar to connector 18 described above), thereby reducing the level of exposure of the severed connector 70. This configuration can prevent or reduce direct contact from the severed third portion 76 with other portions of the stent or adjacent body tissue. Additionally, the thickness of the third portion 76 can be reduced in a radial direction, as defined above, to further shield a patient's vasculature or other tissue from the potentially rough or jagged edges of the severed third portion 76.

As illustrated, the first and second portions 72, 74 can have atraumatic, curved end portions 72b, 74b to protect a patient's vasculature or other tissue and to substantially surround the third portion 76. Further, the edges of the first and second portions 72, 74 can be smooth or rounded to further protect a patient's vasculature or other tissue. Further, as illustrated, depressions or recesses 78 can be formed in the second end portions 72b, 74b surrounding the third portion 76. In some embodiments, the depressions 78 can effectively increase the length of the third portion 76 to increase the flexibility of the third portion 76, while also limiting the exposed length of the third portion 76 after the third portion 76 has been severed. In some cases, the third portion 76 can be configured to rupture at a location at or within the depression 78 to provide further shielding of a rupture zone of the connector 70.

Figure 7:
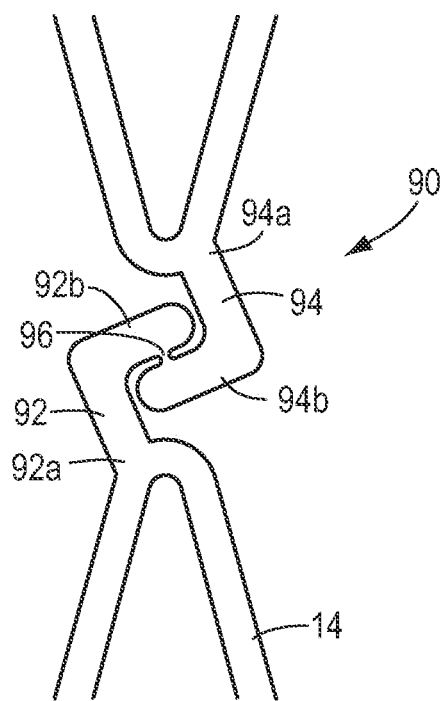
FIG. 7 is an enlarged plan view of another embodiment of a connector.

FIG. 7 is an enlarged plan view of another embodiment of a connector 90. The connector 90 can be used to interconnect any desired portion of adjacent stent segments (having an open or closed cell structure, open serpentine pattern, or otherwise) and are, thus, not limited to interconnecting bistable stent cells as illustrated in some of the figures. In some embodiments, the embodiment of the connector 90 illustrated in FIG. 7 can be configured to sever or break when a predetermined load, level of fatigue, or displacement is experienced by the connector 90, while also being configured to shield adjacent body tissue, stent material, graft material (if the stent is a covered stent), or other adjacent objects from contact with the severed portion of the connector 90 after the connector 90 has severed.

With reference to FIG. 7, the first and second portions 92, 94 of the connector 90 can be configured to partially or fully surround a severable or third portion 96 of the connector 90. In this configuration, after becoming severed, the edges of the severed third portion 96 can be partially or fully surrounded by the first and/or second portions 92, 94, thereby reducing the level of exposure of the severed third portion 96. For example, in some variations, the third portion 96 can be shielded in the axial directions by the first and second portions 92, 94 of the connector 90. In other embodiments, the third portion 96 can be shielded in the radial direction. In other embodiments, the third portion can be shielded in the circumferential direction. In some variations, the third portion 96 can be shielded in the axial, radial, and circumferential directions. This configuration can prevent or reduce direct contact from the severed third portion 96 with other portions of the stent or adjacent body tissue. Additionally, the thickness of the third portion 96 can be reduced in a radial direction to further shield a patient's vasculature or other tissue from the potentially rough or jagged edges of the severed third portion 96.

As illustrated, the first and second portions 92, 94 can have atraumatic, angled end portions 92b, 94b to substantially surround the third portion 96. The angled end portions 92b, 94b advantageously can be oriented such that they are disposed between the ruptured ends of the connector 90 and other portions of the stent or adjacent body tissue to prevent or reduce direct contact from the ruptured ends with other portions of the stent or adjacent body tissue. This arrangement can limit interactions between a severed portion of the connector 90 and stent cells or other structures providing scaffolding of the vessel. Further, the edges of the first and second portions 92, 94 can be smooth or rounded to provide greater protection to a patient's vasculature or other tissue.

Figure 8:
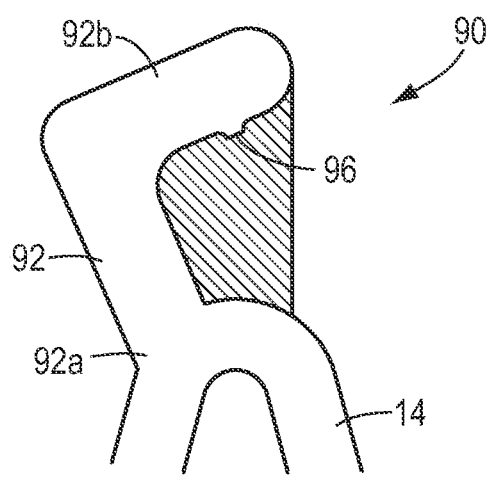
FIG. 8 is a schematic illustration of the zone or pocket of protection provided to the severed portion of the connector by each of the first and second portions of the connector illustrated in FIG. 7.

FIG. 8 is a schematic illustration of the zone or pocket of protection provided to the severed third portion 96 of the connector 90 by the first portion 92 of the connector 90 illustrated in FIG. 6. The zone or pocket of protection is schematically illustrated as the cross-hatched area surrounding the third portion 96 of the connector 90. In some embodiments, the zone of protection projects from the distal end of the second portion 92b toward the stent cell 14 and represents the area or zone of protection surrounding the severed third portion 96 provided by the angled end portion 92b of the first portion 92 of the connector 90. In other words, the angled end portion 92b of the first portion 92 partially surrounds the severed third portion 96 to inhibit or prevent adjacent stent portions or other objects from projecting into the zone of protection. The embodiment of the second portion 94 illustrated in FIG. 6 is similarly configured.

Figure 9:
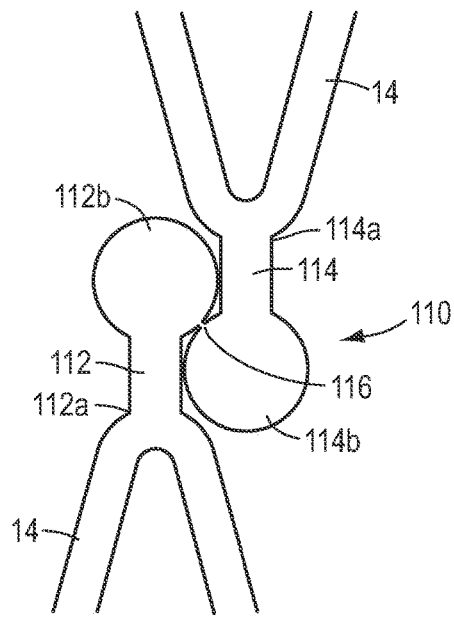
FIG. 9 is an enlarged plan view of another embodiment of a connector.

FIG. 9 is an enlarged plan view of another embodiment of a connector 110. The connector 110 can be used to interconnect any desired portion of adjacent stent segments (having an open or closed cell structure, open serpentine pattern, or otherwise) and are, thus, not limited to interconnecting bistable stent cells as illustrated in some of the figures.

With reference to FIG. 9, the first and second portions 112, 114 of the connector 110 can be configured to partially or fully surround a severable or third portion 116 of the connector 110 such that, after becoming severed, the potentially rough or jagged edges of the severed third portion 116 are shielded from the anatomy or adjacent portions of the stent. The third portion can be shielded by being partially or fully surrounded in the axial, radial, and/or circumferential directions (similar to connector 18 described above), thereby reducing the level of exposure of the severed connector 110 with adjacent tissue or stent portions. Additionally, the thickness of the third portion 116 can be reduced in a radial direction to prevent or reduce direct contact from the severed third portion 116 with other portions of the stent or adjacent body tissue.

As illustrated, the first and second portions 112, 114 can have atraumatic, round end portions 112b, 114b, similar to the geometry of a stent with radiopaque markers, to further protect a patient's vasculature or other tissue and to substantially surround the third portion 116. In one embodiment, at least one of the end portions 112b, 114b comprises a radiopaque marker and the third portion 116 is disposed between the portions 112b, 114b. For example, the third portion 116 can comprise a structure is located on a distal facing edge of a proximal portion of the end portion 112b. The third portion 116 can comprise a structure that is located on a proximal facing edge of the end portion 114b. In one embodiment, the third portion 116 comprises a structure that extends between a generally proximal facing edge of a proximally located cell and a generally distal facing portion of a distal cell, where the proximal facing edge of the proximal cell is located distal of the distal facing edge of the distal cell in a delivery state. Further, the edges of the first and second portions 112, 114 can be smooth or rounded to further protect a patient's vasculature.

Figure 10:
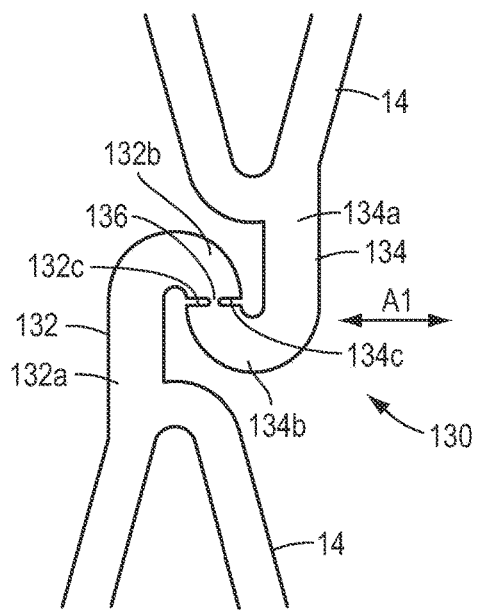
FIG. 10 is an enlarged plan view of another embodiment of a connector.

FIG. 10 is an enlarged plan view of another embodiment of a connector 130. The connector 130 can be used to interconnect any desired portion of adjacent stent segments (having an open or closed cell structure, open serpentine pattern, or otherwise) and are, thus, not limited to interconnecting bistable stent cells as illustrated in some of the figures.

With reference to FIG. 10, the first and second portions 132, 134 of the connector 130 can be configured to partially or fully surround a severable or third portion 136 of the connector 130 such that, after becoming severed, the potentially rough or jagged edges of the severed third portion 136 are shielded from the anatomy or adjacent portions of the stent. The third portion can be shielded by being partially or fully surrounded in the axial, radial, and/or circumferential directions (similar to connector 18 described above), thereby reducing the level of exposure of the severed connector 130. This configuration can prevent or reduce direct contact from the severed third portion 136 with other portions of the stent or adjacent body tissue. Additionally, the thickness of the third portion 136 can be reduced in a radial direction to prevent or reduce direct contact from the severed third portion 136 with other portions of the stent or adjacent body tissue.

As illustrated, the first and second portions 132, 134 can have atraumatic, curved portions adjacent to the end portions 132b, 134b to further protect a patient's vasculature or other tissue and to substantially surround the third portion 136. The edges of the first and second portions 132, 134 can be smooth or rounded to further protect a patient's vasculature or other tissue. Further, the end surfaces 132c, 134c of the first and second portions 132, 134 can be oriented in a circumferential direction (the circumferential direction being indicated by arrow A1 in FIG. 10). The third portion 136 can be oriented in a direction that is normal to the end surfaces 132c, 134c of the first and second portions 132, 134. In one embodiment, the third portion 136 extends generally parallel to a longitudinal axis of a stent of which a portion is shown in FIG. 10. In this configuration, the smallest cross-sectional area of the third portion 136 is defined by a plane that is normal to the longitudinal axis of the stent.

Figure 11:
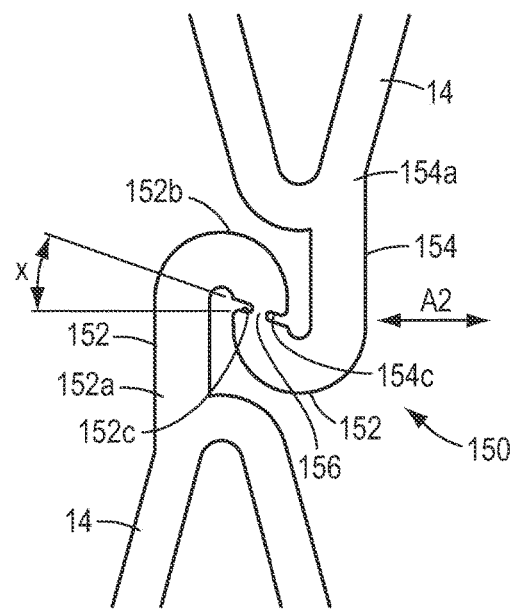
FIG. 11 is an enlarged plan view of another embodiment of a connector.

FIG. 11 is an enlarged plan view of another embodiment of a connector 150. The connector 150 is similar to those hereinbefore described, e.g., FIG. 10, except as described differently below and can be used in a wide variety of applications as discussed above.

As illustrated, first and second portions 152, 154 can have atraumatic, curved portions adjacent to the end portions 152b, 154b to further protect a patient's vasculature or other tissue and to substantially surround a severable or third portion 156. The end surfaces 152c, 154c of the first and second portions 152, 154 can be oriented in an angular direction defined by angle X relative to the circumferential direction of the stent (the circumferential direction being indicated by arrow A2 in FIG. 11). The third portion 156 can be oriented in a direction that is normal to the end surfaces 152c, 154c of the first and second portions 152, 154.

In some embodiments, the angle X can be approximately 25 degrees. However, in some embodiments, the angle X can be from approximately 10 degrees or less to approximately 45 degrees or more, or from approximately 20 degrees to approximately 35 degrees, or to or from any values within these ranges.

Figure 12:
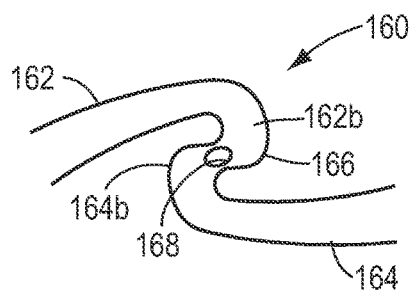
FIG. 12 is an enlarged plan view of another embodiment of a connector.

FIG. 12 is an enlarged plan view of another embodiment of a connector 160. FIGS. 13-17 are enlarged plan views of other embodiments of connectors. In some embodiments, the connectors shown in FIGS. 13-17 can have any of the same features of the embodiment of the connector shown in FIG. 12, except as described below.

The connector 160 can be used to interconnect any desired portion of adjacent stent segments or stent cells (not illustrated). In some embodiments, the embodiment of the connector 160 illustrated in FIG. 12 can be configured to sever or break when a predetermined load, level of fatigue, or displacement is experienced by the connector 160, while also being configured to shield adjacent body tissue, stent material, or other adjacent objects from contact with the severed portion of the connector 160 after the connector 160 has severed.

With reference to FIG. 12, the first and second portions 162, 164 of the connector 160 can be configured to partially or fully surround a severable or third portion 166 of the connector 160. In this configuration, after becoming severed, the edges of the severed third portion 166 can be partially or fully surrounded by the first and/or second portions 162, 164, thereby reducing the level of exposure of the severed third portion 166. For example, in some variations, the third portion 166 can be shielded in any one or more of the axial, radial, and circumferential directions by the first and second portions 162, 164 of the connector 160. This configuration can prevent or reduce direct contact from the severed third portion 166 with other portions of the stent or adjacent body tissue. Additionally, the thickness of the third portion 166 can be reduced in a radial direction to further shield a patient's vasculature or other tissue from the potentially rough or jagged edges of the severed third portion 166.

As illustrated, the first and second portions 162, 164 can each have looped or curved end portions 162b, 164b to substantially surround the third portion 166. The curved end portions 162b, 164b advantageously can be oriented such that they are disposed between the ruptured ends of the connector 160 and other portions of the stent or adjacent body tissue to prevent or reduce direct contact from the ruptured ends with other portions of the stent or adjacent body tissue after the third portion 166 has been severed. This arrangement can limit interactions between a severed portion of the connector 160 and stent cells or other structures providing scaffolding of the vessel. Further, the edges of the first and second portions 162, 164 can be smooth or rounded to provide greater protection to a patient's vasculature or other tissue.

Additionally, with reference to FIG. 12, the third portion 166 can have one or more openings 168 (one being illustrated) formed through the connector 160. In some embodiments, the opening 168 can be oriented in a radial direction relative to the stent. Alternatively, the opening 168 can be oriented in a circumferential or a longitudinal direction relative to the stent. The opening 168 can be sized and configured to reduce the cross-sectional area of the third portion 166, so that the third portion 166 is designed to break or sever under a predetermined level of cyclic fatigue, a predetermined load, or a predetermined displacement.

In some embodiments, as in the illustrated embodiment, the opening 168 can be located in the approximate widthwise center of the third portion 166 of the connector 160. In other embodiments, the opening 168 can be off-center, or positioned adjacent to one of the side surfaces of the third portion 166 so as to be open on one side, similar to the opening 178 of the connector 170 illustrated in FIG. 13.

Figure 13:
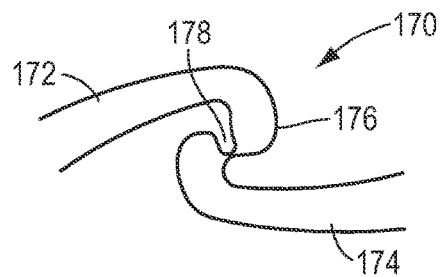
FIG. 13 is an enlarged plan view of another embodiment of a connector.
Figure 15:
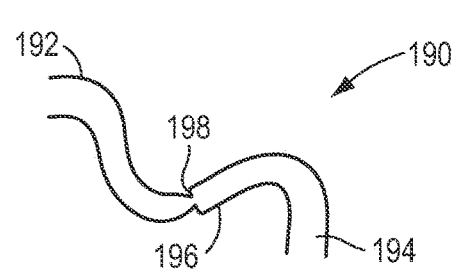
FIG. 15 is an enlarged plan view of another embodiment of a connector.
Figure 16:
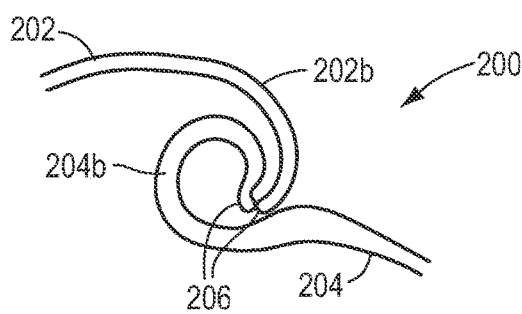
FIG. 16 is an enlarged plan view of another embodiment of a connector.

In some embodiments, as in the illustrated embodiment, the opening 168 can have a generally circular shape, as illustrated in FIG. 12. In other embodiments, the opening can have a generally square shape, as illustrated in FIG. 13, or any other generally rectangular, ovular, triangular, slit-like, or other suitable shape. In some embodiments, the connector can have more than one opening formed therein, such as with the embodiment of the connector 190 illustrated in FIG. 15. With reference to FIG. 15, two generally triangular openings 198 can be formed in the connector 190, each being adjacent to the opposing side surfaces of the third portion 196 of the connector 190.

Figure 14:
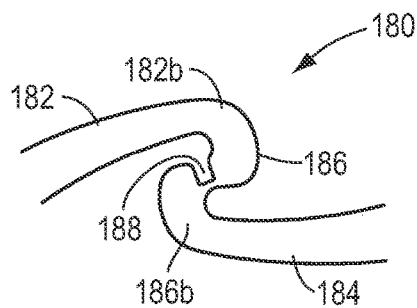
FIG. 14 is an enlarged plan view of another embodiment of a connector.

FIGS. 13-15 also illustrate that in some embodiments, a portion of a connector can be configured with a reduction in cross-sectional area, such as by providing a recess in the connector to reduce the width at a location between the ends of the connector. In these embodiments, the reduction in width can be due to an incursion from a side of the connector portion toward a middle portion of the connector. In contrast, in the embodiment of FIGS. 12 and 17 (discussed below), a through-hole can be provided in a mid-portion of a length of the connector to reduce the amount of material in cross-section at a specific location along the length of the connector. In some embodiments, rather than a through-hole or incursion creating a recess, the material can be thinned to reduce the cross-sectional area of the material, thus providing a pre-selected facture zone in the connector.

FIG. 14 is an enlarged plan view of another embodiment of a connector 180. As illustrated, the connector 180 can have generally curved first and second portions 182, 184, and a generally square or rectangular opening 188 formed in a third portion 186 of the connector 180. The curvature of the first and second end portions 182b, 184b can be more gradual than in the embodiment of the connector 170 illustrated in FIG. 13 so that the third portion 186 maintains a more circumferential orientation than the third portion 176.

In some embodiments, the curvature of the end portions of the first and second segments of the connector can be more pronounced or spiral-like or otherwise provide multiple areas of overlap in a longitudinal or other direction of the stent. For example, with reference to FIG. 16, in some embodiments, the end portion 204b of the second portion 204 of the connector can form a nearly complete, but open, loop or spiral. As with other embodiments, a third portion 206 of the connector can be positioned adjacent to the ends of the first and second portions 202, 204 of the connector 206. The third portion 206 can have a reduced cross-section as compared to the first and second portions 202, 204, or can have a similarly sized cross-section as compared to the first and second portions 202, 204.

Figure 17:
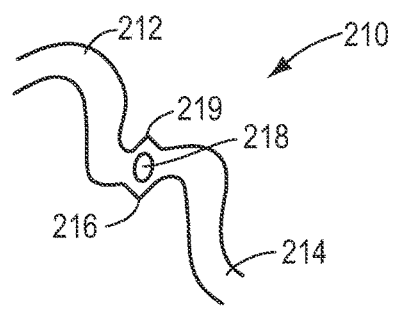
FIG. 17 is an enlarged plan view of another embodiment of a connector.

In some embodiments, as illustrated in FIG. 17, the third portion 216 of the connector 210 can have an opening 218 therein, the opening being approximately centered with respect to an enlarged portion 219 of the third portion 206 of the connector 210. In some embodiments, as in the illustrated embodiment, the enlarged portion 219 of the connector 210 can be approximately triangular shaped, and the opening 218 can be approximately circular shaped. Also, the embodiment of FIG. 17 provides an arrangement in which the opening 218 (which can be a thinning of the connector rather than a complete through-hole) has a width that is equal or substantially equal to the width of adjacent portions of the connector. The enlarged portion 219 is provided to temporarily bridge from a distal connector portion to a proximal connector portion. For example, in some embodiments discussed herein the connector comprises a first portion, a second portion, and third portion disposed between the first and second portions. The first and second portions need not be clearly structurally separate or separable stent portions, but rather can be a length of the connector extending from adjacent to a point of connection with cells on either side of the connector. For example, the first portion can be coupled at one end with a distal stent cell and extend a length generally proximally therefrom and the second portion can be coupled at one end with a proximal stent cell and extend a length generally distally therefrom. In the embodiment of FIG. 17, the enlarged portion 219 can bridge between the first and second portions of the connector. The enlarged portion 219 also can border the opening 218.

Figure 18:
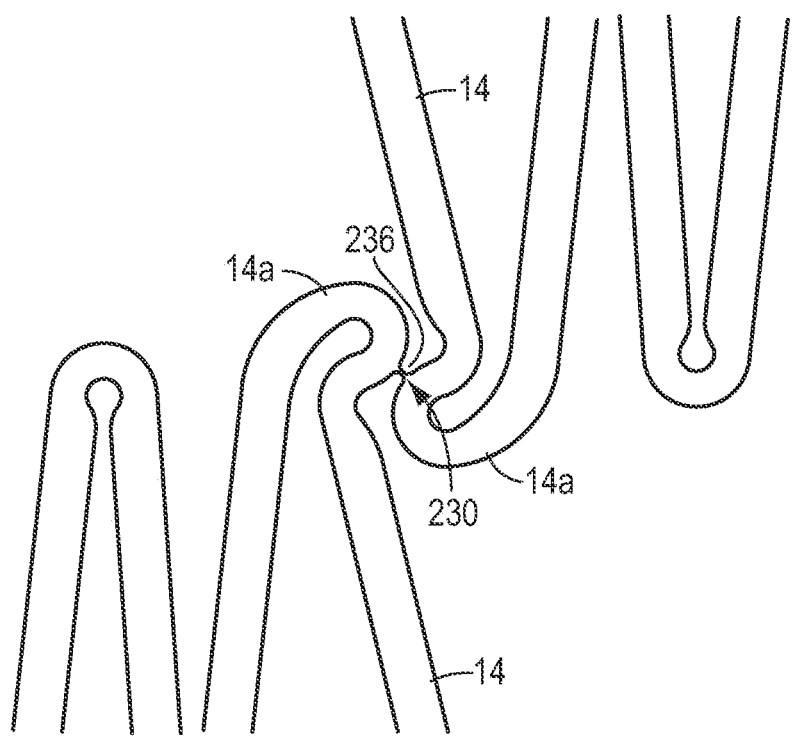
FIG. 18 is an enlarged plan view of another embodiment of a stent having a connector between two portions of a stent cell or segment.

FIG. 18 is an enlarged plan view of another embodiment of a connector 230, wherein the severable portion 236 of the connector 230 is directly supported by the adjacent stent cells 14. The connector 230 can be used to interconnect any desired portion of adjacent stent segments (having an open or closed cell structure, open serpentine pattern, or otherwise) and is, thus, not limited to interconnecting the type of stent cells illustrated in FIG. 18.

With reference to FIG. 18, the stent cells 14 can be configured to partially or fully surround a severable portion 236 of the connector 230 such that, after becoming severed, the potentially rough or jagged edges of the severed severable portion 236 are shielded from the anatomy or adjacent portions of the stent. The third portion can be shielded by being partially or fully surrounded in the axial, radial, and/or circumferential directions, thereby reducing the level of exposure of the severed portion 230. For example, as illustrated, the end portions 14a of each of the stent cells 14 can be curved and otherwise configured to partially surround the severable portion 236 of the connector 230. This configuration can prevent or reduce direct contact from the severed third portion 236 with other portions of the stent or adjacent body tissue. Additionally, the thickness of the severable portion 236 can be reduced in a radial direction to further shield a patient's vasculature or other tissue from the potentially rough or jagged edges of the severed severable portion 236.

Figure 19A:
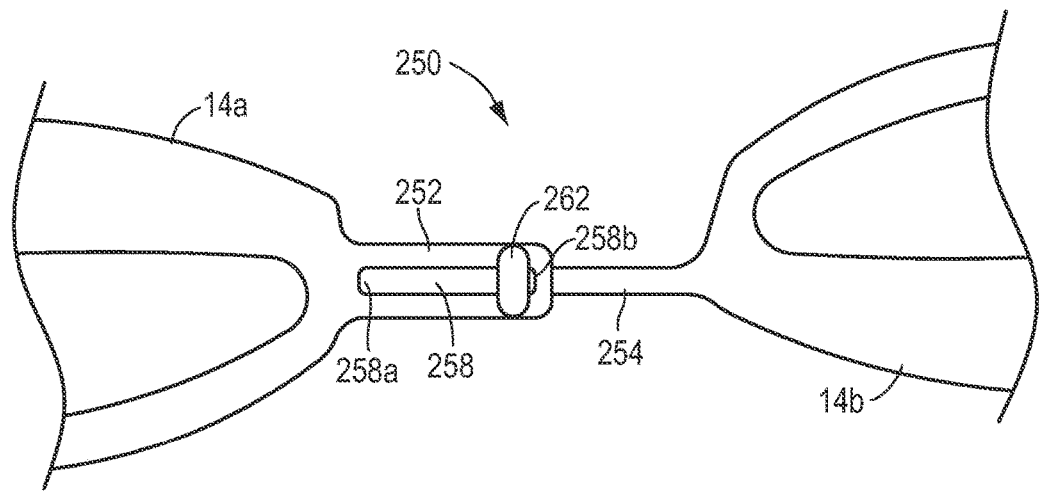
FIG. 19A is an enlarged view of another embodiment of a connector, showing the connector in a first or extended position.

FIG. 19A is an enlarged view of another embodiment of a connector 250 that can be used with any of the stents disclosed herein, showing the connector 250 in a first or extended position. For example, without limitation, the connector 250 can be used in place of some or all of the connectors 18 for the stent 10 described above. Any of the stents disclosed or incorporated by reference herein can comprise any number, combination, or configuration of the connector embodiments disclosed herein. Further, the connector 250 or any other connector disclosed herein can be used to interconnect any desired portion of adjacent stent segments (having an open or closed cell structure, open serpentine pattern, or otherwise) and are, thus, not limited to interconnecting bistable stent cells as illustrated in some of the figures.

With reference to FIG. 19A, the connector 250 can be used to interconnect a first stent cell 14a with a second stent cell 14b. The connector 250, or any connector disclosed herein, can be positioned at any desired location on the stent segment. As illustrated in FIG. 19A, the connector 250 is positioned approximately at the apex of each of the stent cells 14a, 14b. The connector 250, or any other connectors disclosed herein, can be positioned off-center from the apex of the cells or bends in the case of serpentine or open cell designs, closer to the thicker strut of the stent cells, off-center from the apex of the stent cells or bends in the case of serpentine or open cell designs, or otherwise. Further, the stent cells 14a, 14b can be arranged in any desired orientation, including the arrangement shown in FIG. 19A in which the stent cells 14a, 14b are arranged in opposite orientations. In one embodiment, the cells are asymmetrical about a longitudinal axis and adjacent cells along the length of the stent are oriented 180 degrees from each other about the longitudinal axis. For example, in one embodiment, the cells each comprise a circumferentially wider strut and a circumferentially narrower strut and adjacent cells are oriented such that the circumferentially wider struts are on opposite sides of the longitudinal axis. In FIG. 19A, the strut 14a is circumferentially wider than the strut 14b and the struts 14a, 14b are located on opposite sides of a longitudinal axis extending generally long the length of the connector 250.

The connector 250 can have a first portion 252 and a second portion 254 slidably engaged with the first portion 252. As illustrated, the first portion 252 can define a longitudinal opening 258 having a first end portion 258a and a second end portion 258b. The longitudinal opening 258 can be configured to slidably receive at least a portion of the second portion 254 so as to compensate for any foreshortening or lengthening, or axial compressive or tensile forces exerted on the stent 250. The second portion 254 can have a tab 262 positioned at a distal portion of the second portion 254. The tab 262 can have a size larger than the width of the longitudinal opening 258, or otherwise be configured to prevent the second portion 254 from becoming disengaged from the first portion 252. The tab 262 can face either radially outward (e.g., on the outside surface of the stent, as illustrated) or radial inward (e.g., on the inside surface of the stent), or otherwise be configured so that interference with a cover or body tissue (such as the vessel wall) is minimized.

Figure 19B:
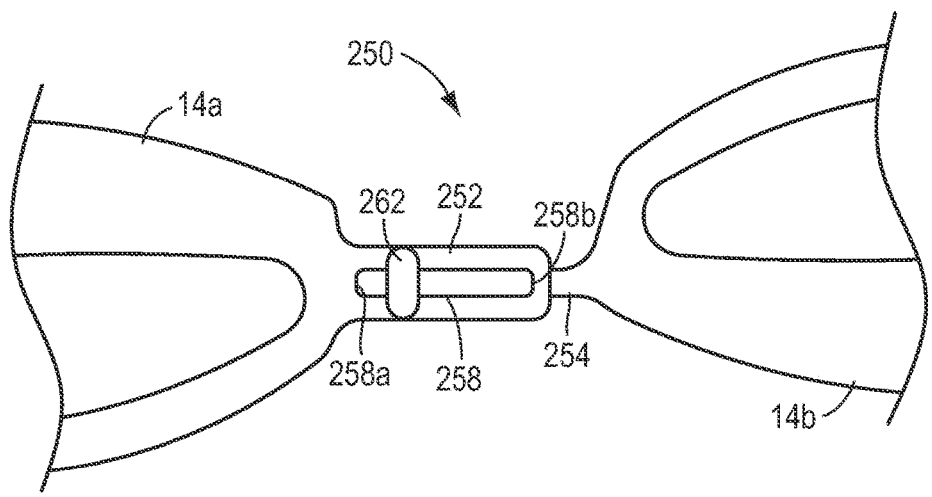
FIG. 19B is an enlarged view of the embodiment of the connector shown in FIG. 13A, showing the connector in a second or contracted position.

FIG. 19B is an enlarged view of the embodiment of the connector shown in FIG. 19A, showing the stent portion to which the connector is coupled in a second or contracted position. As illustrated in FIG. 19B, the stent cells 14a, 14b have moved more closely together, which can compensate for compressive forces from bending, or from foreshortening of the vessel in which the stent is deployed or otherwise. The connector 250 also can move from the second position of FIG. 19B to the first position of FIG. 19A to compensate for foreshortening of the cells 14a, 14b and thus minimize foreshortening of the stent in some embodiments. The first and second portions 252, 254 can define any desired size or configuration, so as to accommodate a wide range of desired translation distances.

In some embodiments, the first portion 252 can be defined by a generally tubular shape having a longitudinal opening therein configured to slidably receive the second portion 254. Either or both of the first and second portions 252, 254 can comprise detents, protrusions, channels, or other features configured to limit the range of translation of the second portion 254 relative to the first portion 252, or otherwise be configured such that the second portion 254 is at least inhibited from becoming disengaged from the first portion 252 of the connector 250.

Figure 20A:
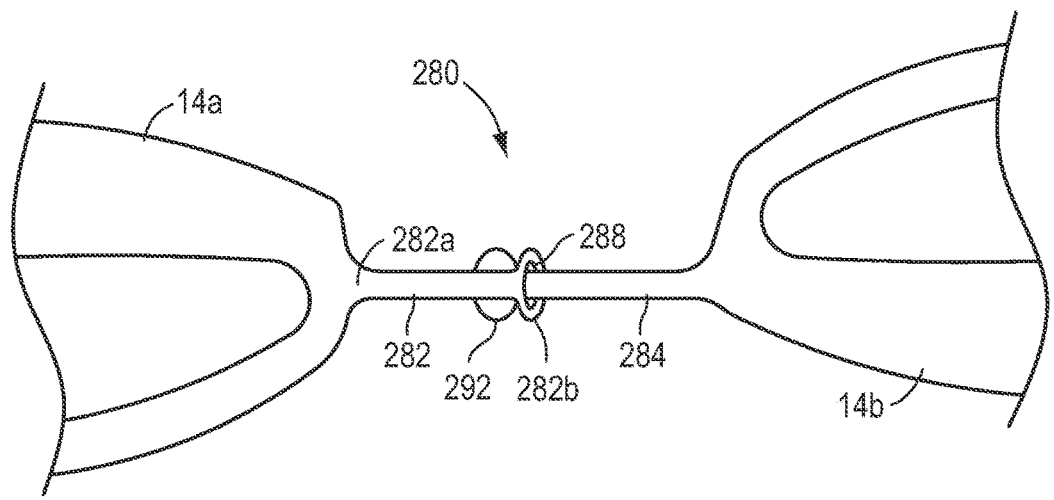
FIG. 20A is an enlarged view of another embodiment of a connector, showing the connector in a first or extended position.

FIG. 20A is an enlarged view of another embodiment of a connector 280 that can be used with any of the stents disclosed herein, showing the connector 280 in a first or extended position. For example, without limitation, the connector 280 can be used in place of some or all of the connectors 28 for the stent 10 described above. Any of the stents disclosed or incorporated by reference herein can comprise any number, combination, or configuration of the connector embodiments disclosed herein. Further, connector 280 or any other connector disclosed herein can be used to interconnect any desired portion of adjacent stent segments (having an open or closed cell structure, open serpentine pattern, or otherwise) and are, thus, not limited to interconnecting bistable stent cells as illustrated in some of the figures.

With reference to FIG. 20A, the connector 280 can be used to interconnect a first stent cell 14a with a second stent cell 14b. The connector 280, or any connector disclosed herein, can be positioned at any desired location on the stent segment. As illustrated in FIG. 20A, the connector 280 is positioned approximately at the apex of each of the stent cells 14a, 14b. The connector 280, or any other connectors disclosed herein, can be positioned off-center from the apex of the cells or bends in the case of serpentine or open cell designs, closer to the thicker strut of the stent cells, off-center from the apex of the stent cells or bends in the case of serpentine or open cell designs, or otherwise. Further, the stent cells 14a, 14b can be arranged in any desired orientation, including the arrangement shown in FIG. 20A in which the stent cells 14a, 14b are arranged in opposite orientations.

The connector 280 can have a first portion 282 and a second portion 284 slideably engaged with the first portion 282. As illustrated, the first portion 282 can define an opening 288 at a distal or second end 282b of the first portion 282. In some embodiments, the second end portion 282b of the first portion 282 can be configured to project radially inwardly such that the opening 288 is oriented in an axial direction so that the second portion 284 can project through the opening in an axial direction.

The opening 288 can be configured to slidably receive at least a portion of the second portion 284 so as to compensate for foreshortening or lengthening, or axial compressive or tensile forces exerted on the stent 280. The second portion 284 can have a tab 292 positioned at a distal portion of the second portion 284. The tab 292 can have a size larger than a width or other dimension of the opening 288, or otherwise be configured to prevent the second portion 284 from becoming disengaged from the first portion 282. In this configuration, the second portion 284 of the connector 280 can be permitted to slide on the radially inward side of the first portion 282 of the connector, so that interference with a graft cover or body tissue (such as the vessel wall) is minimized.

Figure 20B:
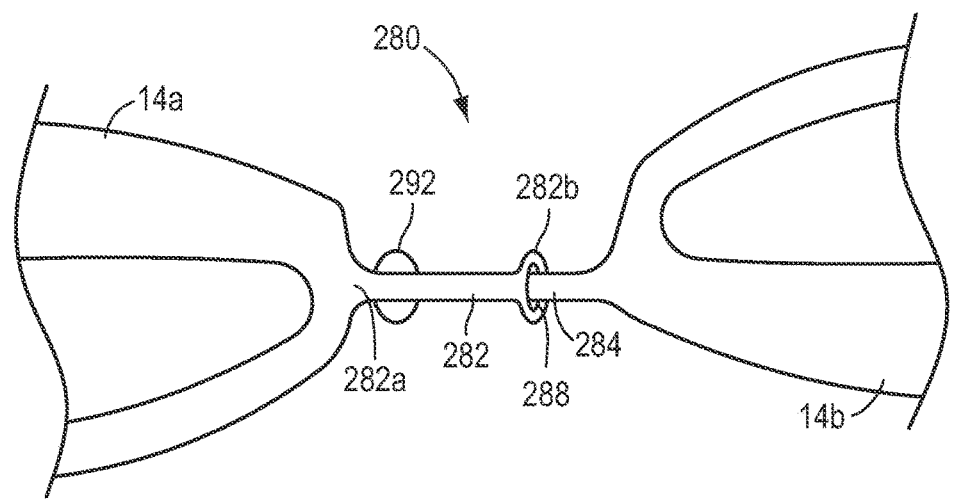
FIG. 20B is an enlarged view of the embodiment of the connector shown in FIG. 5A, showing the connector in a second or contracted position.

FIG. 20B is an enlarged view of the embodiment of the connector shown in FIG. 20A, showing the connector in a second or contracted position. As illustrated in FIG. 20B, the stent cells 14a, 14b have moved more closely together, to compensate for stent axial foreshortening, compressive forces from bending, or otherwise. The first and second portions 282, 284 can define any desired size or configuration, so as to accommodate a wide range of desired translation distances.

Figure 21:
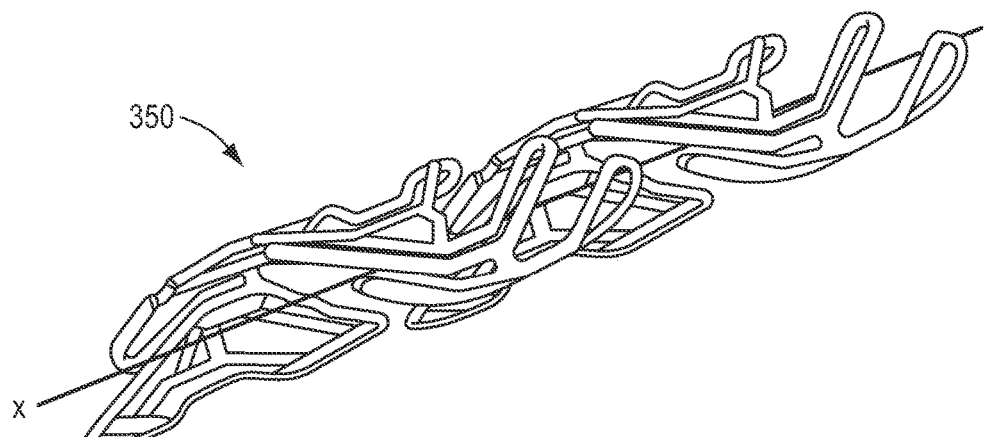
FIG. 21 is a perspective view of an embodiment of a helically arranged stent having one or more severable connectors, showing the stent in a compressed state.
Figure 22:
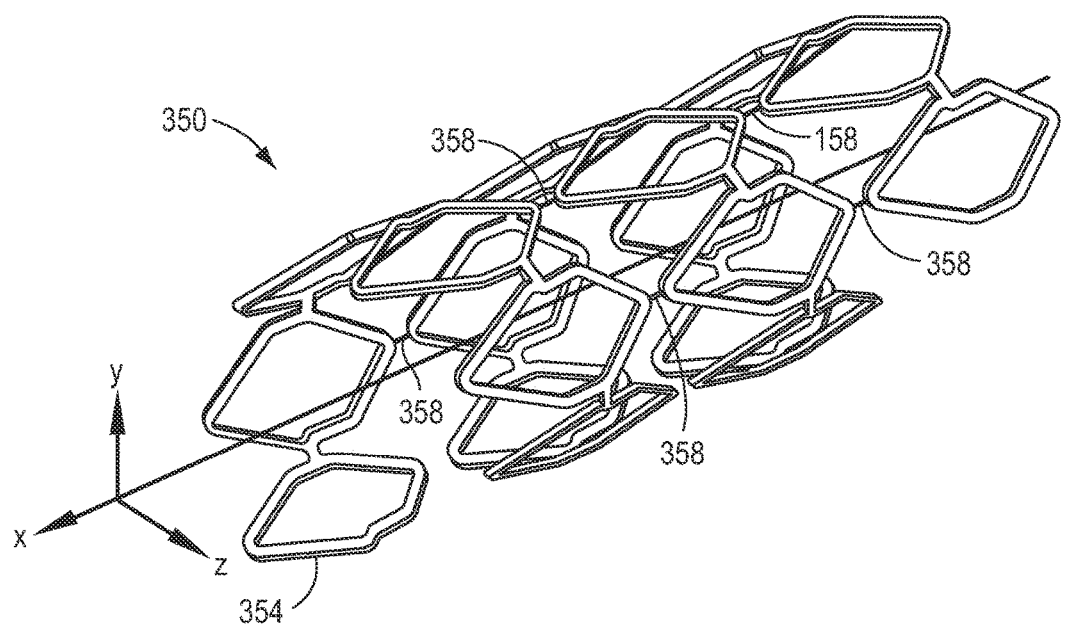
FIG. 22 is a perspective view of an embodiment of a helically arranged stent having one or more severable connectors, showing the stent in an expanded state.

FIGS. 21 and 22 are perspective views of an embodiment of a helically arranged stent 350 having one or more severable connectors 358, showing the stent 350 in a compressed state and an expanded state, respectively. The stent 350 can have any of the same features, configurations, or other details as any of the stent embodiments disclosed in U.S. patent application Ser. No. 11/391,940, filed on Mar. 29, 2006 (entitled "FRACTURE-RESISTANT HELICAL STENT INCORPORATING BISTABLE CELLS AND METHODS OF USE"), which patent application is hereby incorporated by reference as if fully set forth herein. Spiral or helical stents can have a tendency to unravel or stretch or compress in an uncontrolled fashion when deployed. In some embodiments, it may be preferred to have a more axially rigid structure for deployment to maintain good scaffolding and coverage, and to avoid such uncontrolled deployment problems.

Accordingly, the connectors 358 can be arranged in an axial direction between adjacent or closely positioned cells. The embodiments of the axial connectors disclosed herein can be configured to interconnect bistable or non-bistable cells of axially adjacent segments, or to interconnect bistable or non-bistable cells of adjacent helically arranged stents, or otherwise.

Additionally, the connectors 358 can be formed from the same material as the stent cells or any other suitable material, or can be partially or completely formed from a biodegradable or bioabsorbable material as described above. In some embodiments, the connectors 358 can be positioned at any desired helical position, or can be linearly arranged along one or more sides of the stent 350. In this configuration, the connectors 358 can sever when predetermined or threshold compressive, tensile, shear, or torsional forces are imparted on the stent or the connectors.

Figure 23:
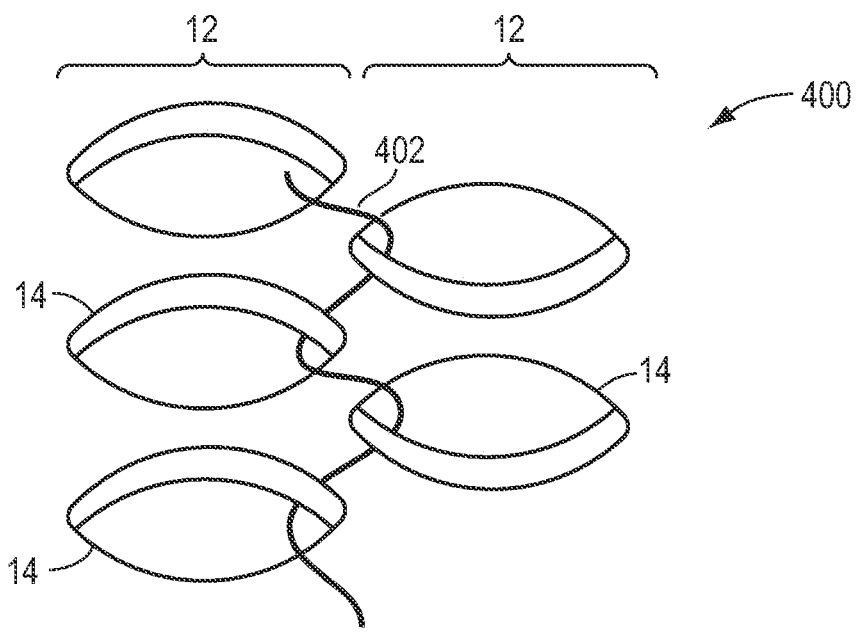
FIG. 23 is a plan view of a portion of a pattern of another embodiment of a stent.

FIG. 23 shows a plan view of an embodiment of a stent 400 having a plurality of stent segments 12 comprising a plurality of stent cells 14. In some embodiments, the stent cells 14 of each segment 12 can be interconnected in a circumferential direction. In use, the stent 400 can define a generally straight or curved cylindrical or tubular shape. The stent 400 can comprise bistable cells, multistable cells, deformable unit cells, open cells, self-expandable cells, balloon or other mechanically expandable cells, any other cells currently known or later developed, or any combination of the foregoing. Further, in some embodiments, the stent segments 12 can have an open stent pattern (serpentine or otherwise) comprising a series of concave and convex bends, or any other suitable structure. In this preferred embodiment, the design eliminates tissue prolapse between rings. The material connecting the rings keeps them oriented such that the apex of each cell alternates with the other. Thus when the 2 rings move or merge together during foreshortening the apices move into the recess between individual cells. This allows some circumferential coverage in the elongated and foreshortened state as shown in 24A.

In some embodiments, one or more adjacent stent segments 12 can be interconnected by one or more wire connectors 402 that can be configured to pass through one or more of the stent cells 14 (as illustrated) or, for open stent patterns (not illustrated), through one or more of the concave or convex bends. The wire connectors 402 can comprise a suitable suture material (biodegradable or otherwise), a metal alloy such as stainless steel or Nitinol, or any other similar or suitable material. In some embodiments, the wire connectors 402 can improve the scaffolding provided to the vessel wall by the stent 400, and can also help maintain the appropriate alignment and spacing of the stent segments 12 during balloon expansion.

Figure 23A:
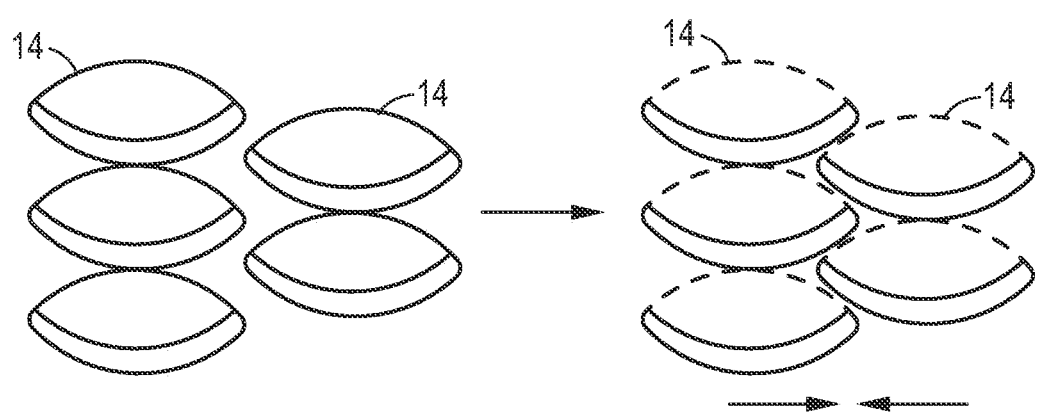
FIG. 23A is a schematic representation of a portion of the pattern of the embodiment of a stent illustrated in FIG. 23, showing the interdigitated stent cells in a relaxed and contracted state.

The wire connectors 402 can be configured to permit a predetermined amount of relative axial, circumferential, or radial displacement between adjacent stent segments 12 to accommodate axial foreshortening or stretching, bending, or other loads or stresses. Some embodiments of the stent cells 14 of one segment 12 can be interdigitated relative to the stent cells 14 of an adjacent segment 12 (as illustrated in FIG. 23A) to increase scaffolding and also accommodate a greater magnitude of axial movement of one stent segment 12 relative to an adjacent stent segment 12.

Additionally, as mentioned, the wire connectors 402 can be formed from a bioabsorbable or biodegradable material that is configured to degrade or be bioabsorbed by the body after a predetermined period of time. In this configuration, the connector can be weakened so as to be more easily severable after a predetermined period of time, or can be completely bioabsorbed so as to remove the connection between adjacent stent segments after a predetermined period of time. Further (not illustrated), in some embodiments, one or more of the adjacent stent segments 12 of the stent 400 can be interconnected by one or more severable connectors of any of the types disclosed herein, in combination with or alternatively to having a wire connector 402 interconnect one or more adjacent stent cells 14 or stent segments 12.

Figure 24A:
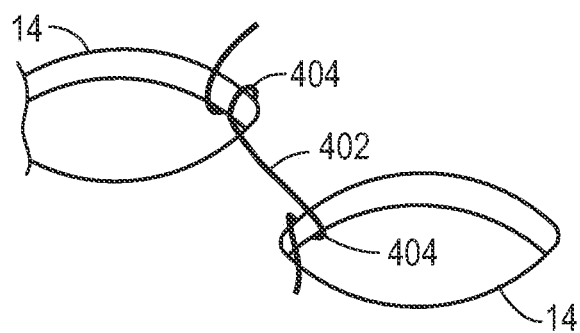
FIG. 24A is a plan view of a portion of another embodiment of a stent having a connector between at least two portions of a stent cell or segment.
Figure 24B:
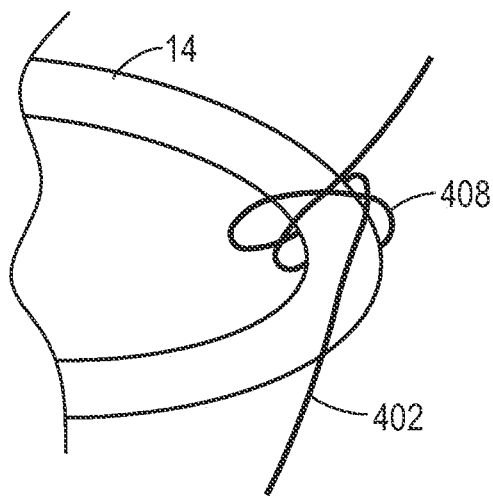
FIG. 24B is a plan view of a portion of another embodiment of a connector configured to provide a connection between at least two portions of a stent cell or segment.
Figure 25:
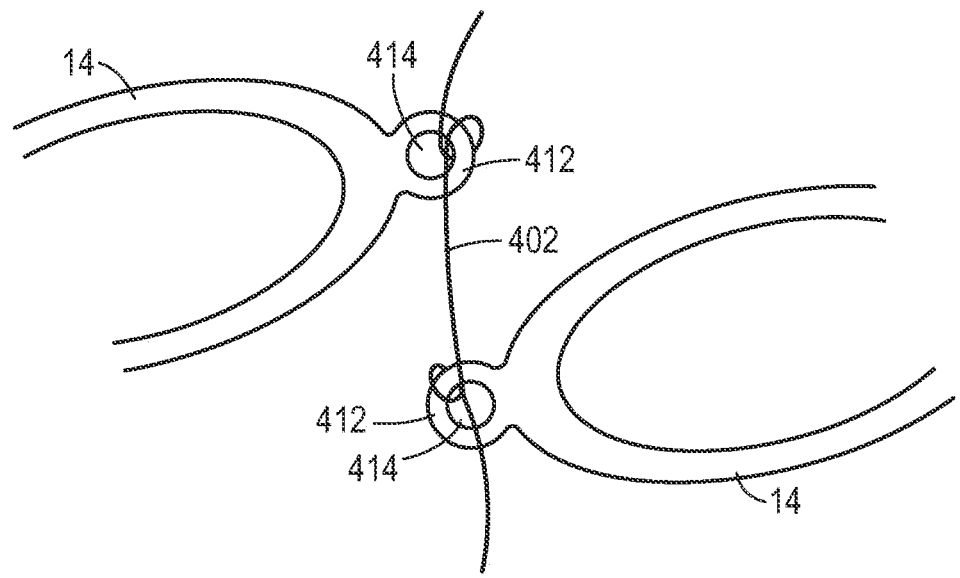
FIG. 25 is a plan view of a portion of another embodiment of a stent having a connector between at least two stent segment portions.
Figure 26:
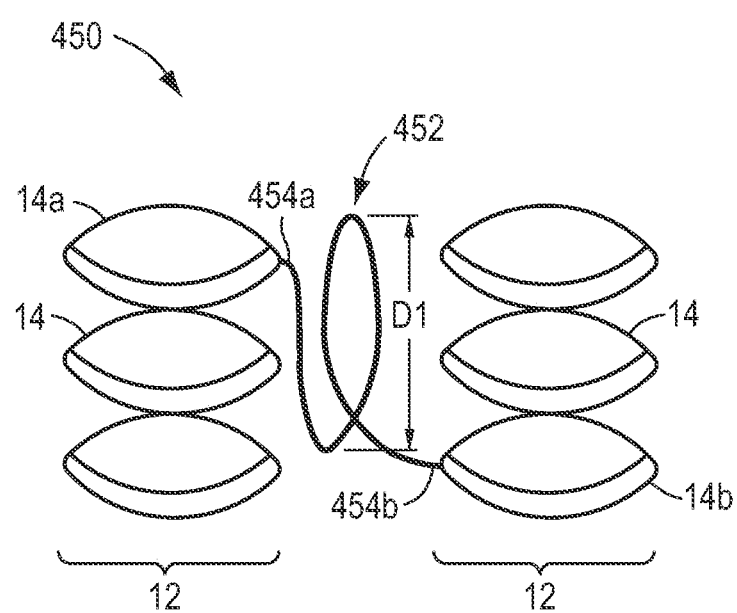
FIG. 26 is a plan view of a portion of another embodiment of a stent having a connector between at least two portions of a stent cell or segment.
Figure 27:
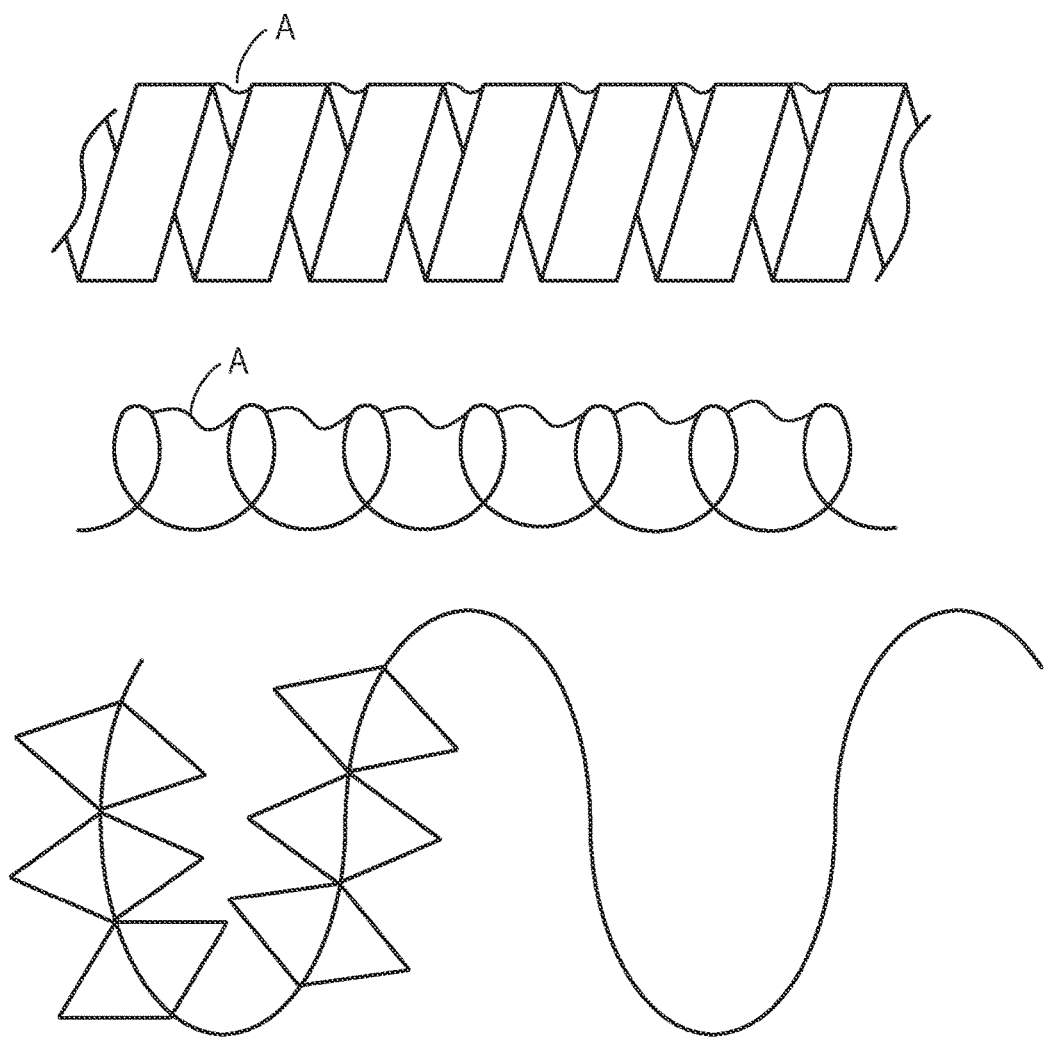
FIGS. 27-37 set forth additional details regarding some embodiments of the stents and connectors disclosed herein.
Figure 28:
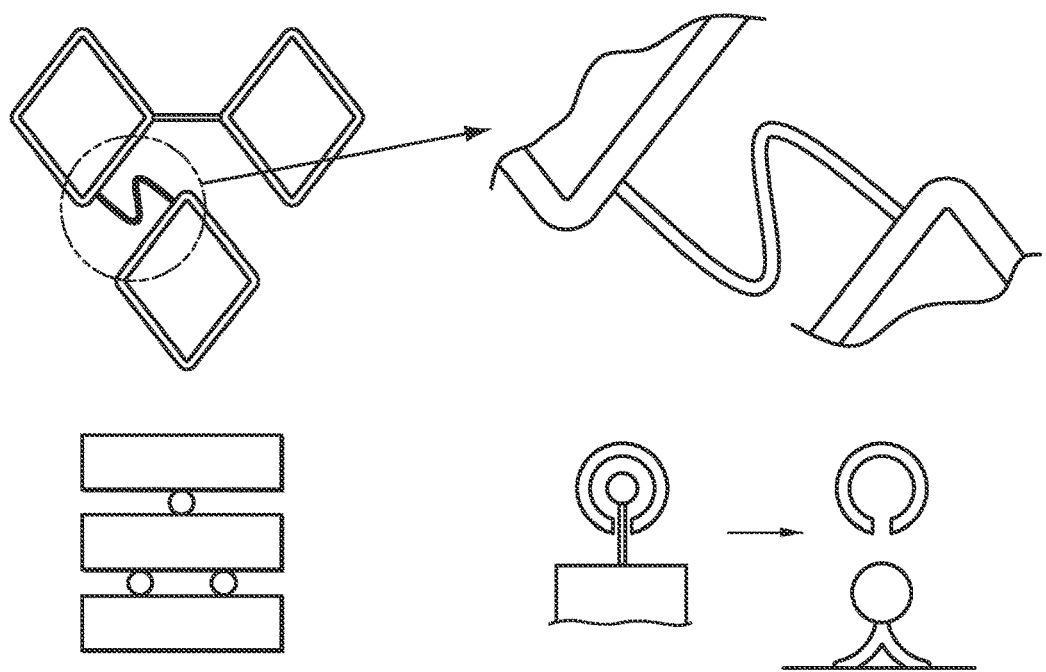
Figure 29:
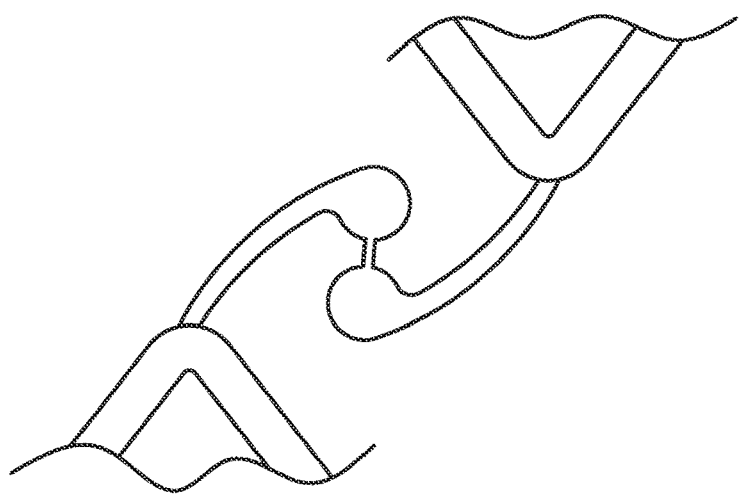
Figure 30:
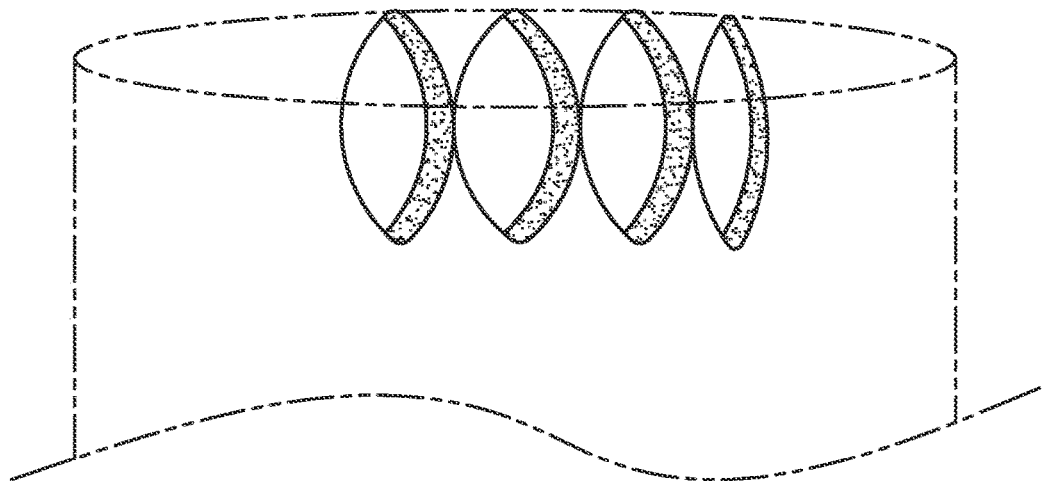
Figure 31:
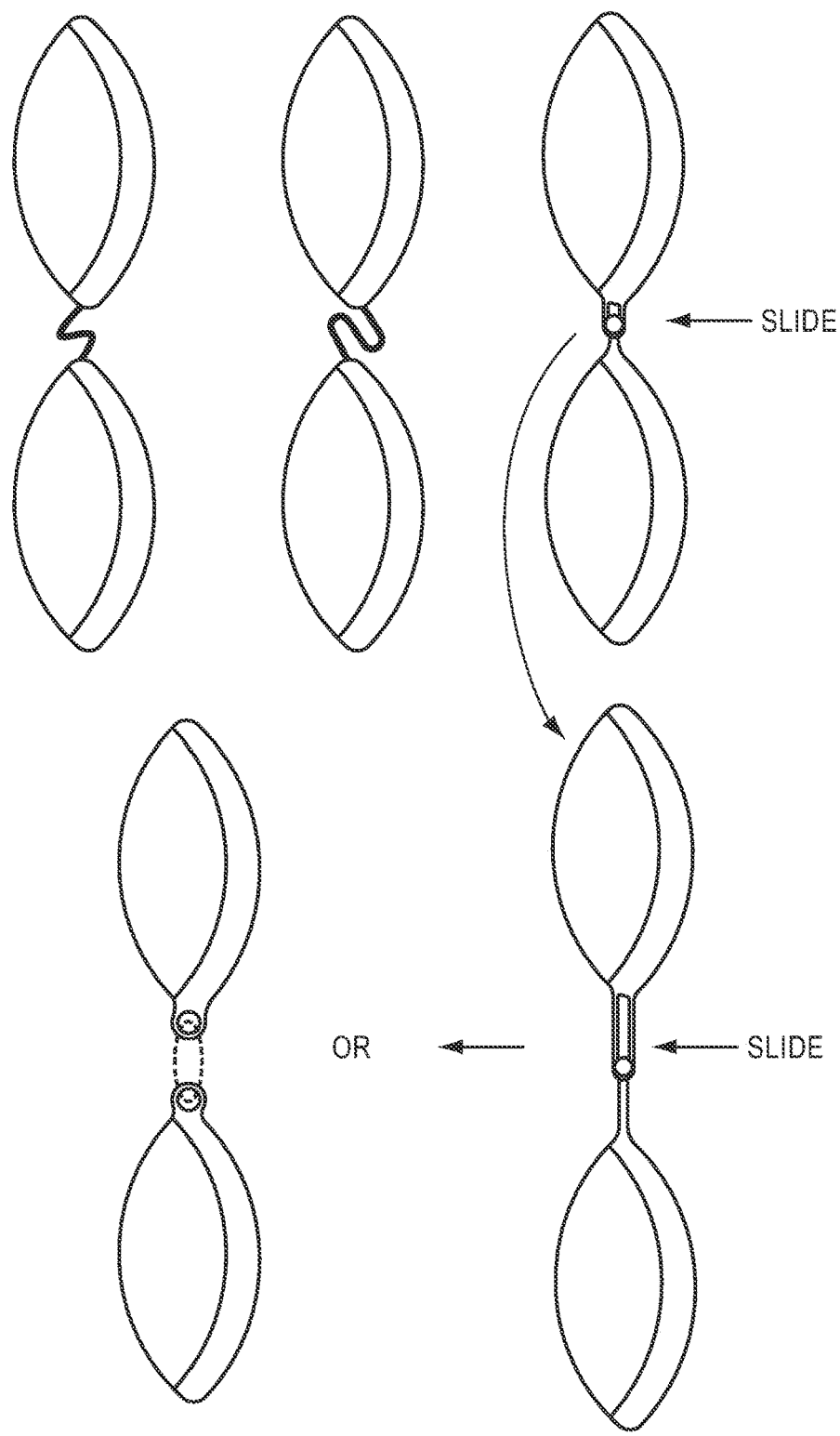
Figure 32:
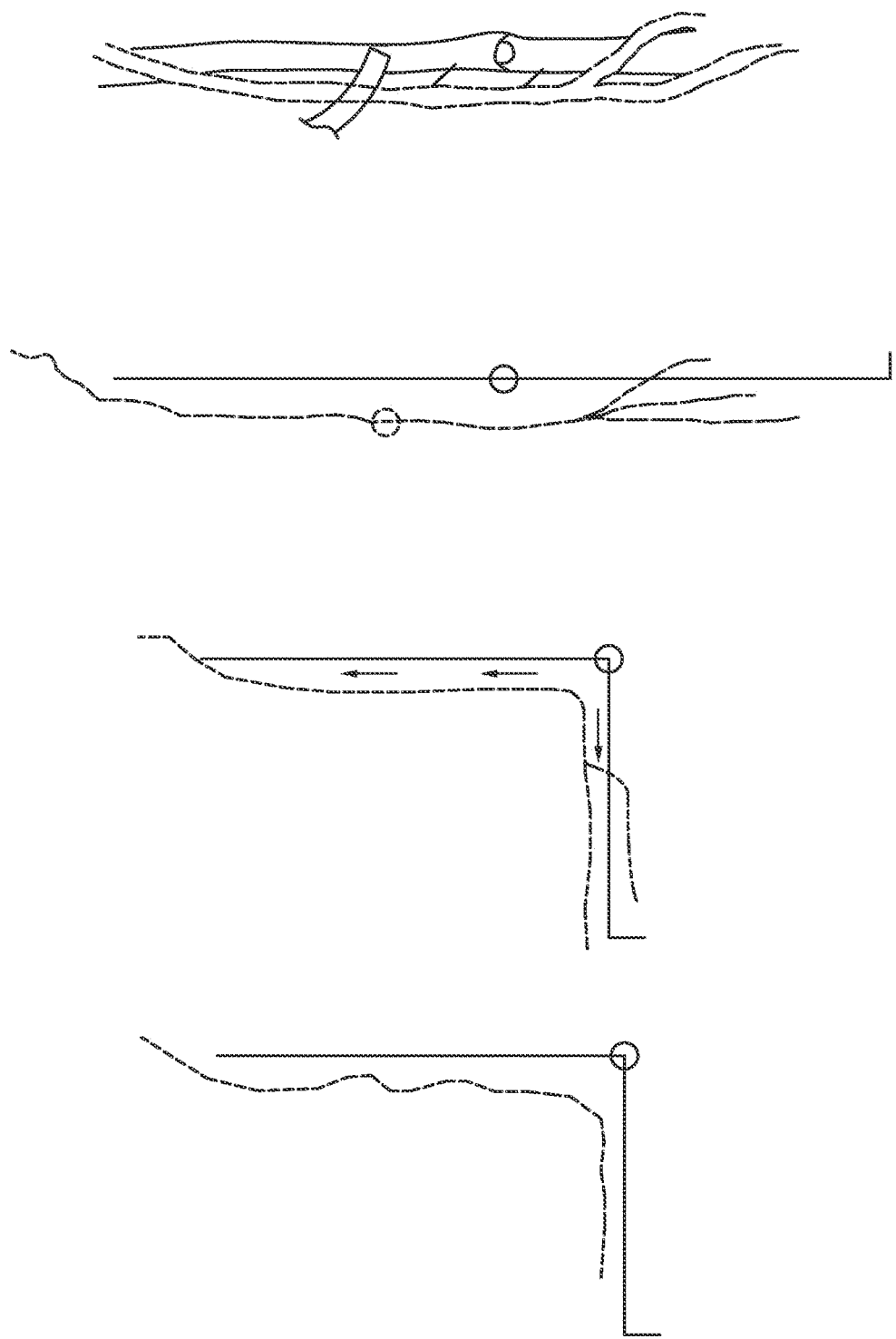
Figure 33:
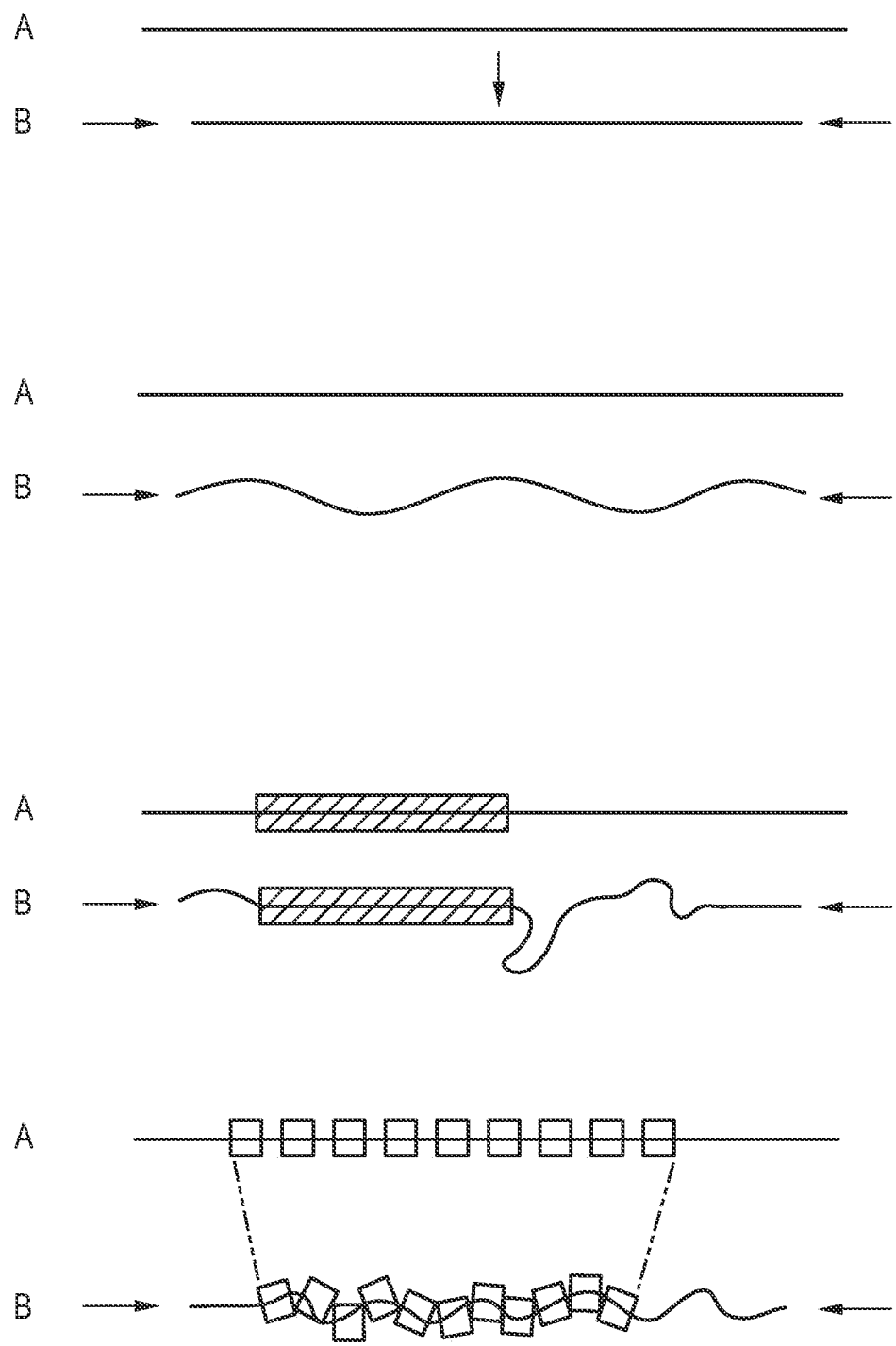
Figure 34:
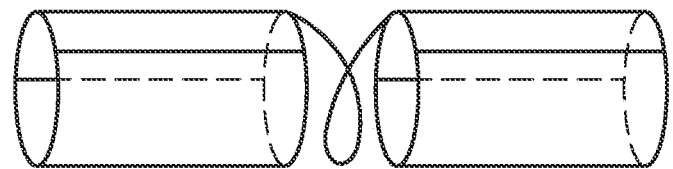
Figure 34:
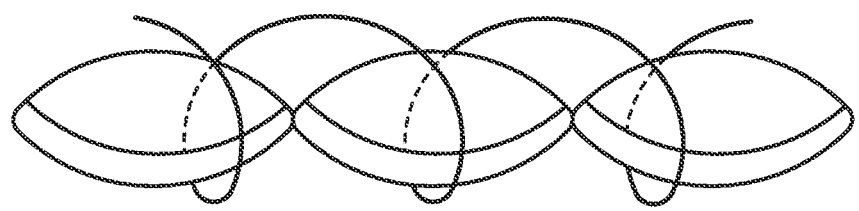
Figure 34:
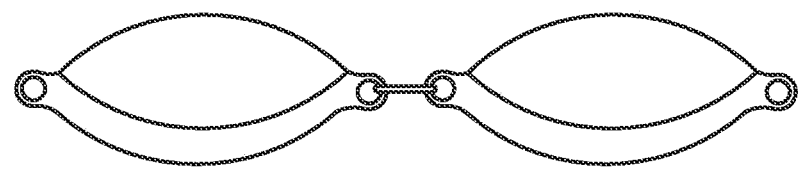
Figure 34:
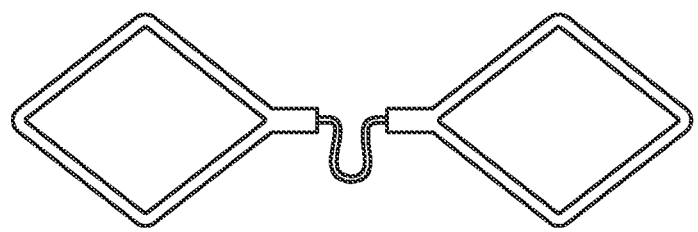

FIGS. 24-25 are plan views of a portion of additional embodiments of a stent having a connector between at least two portions of a stent cell 14 or stent segment 12. In particular, FIGS. 24-26 illustrate different ways in which the wire connector 402 can be joined to or engaged with the stent cells 14 or open cell segments.

In some embodiments, the wire connectors 402 can form a double loop 404 around one or more struts of a stent cell 14 (as illustrated in FIG. 24A) or bends of an open stent structure (not illustrated). In some embodiments, depending on the material comprising the wire connector 402, the double loop 404 can permit some slippage or axial movement of the wire connector 402 relative to the stent cell 14.

In some embodiments, the wire connectors 402 can form a lock knot 408 around one or more struts of a stent cell 14 (as illustrated in FIG. 24B) or bends of an open stent structure (not illustrated). In some embodiments, depending on the material comprising the wire connector 402, the lock knot 408 can substantially inhibit or prevent slippage or axial movement of the wire connector 402 relative to the stent cell 14. In some embodiments, any combination of double loops 404 or lock knots 408 can be used to interconnect one or more adjacent stent cells 14 or stent segments 12. The connector 402 preferably prevents out-of-phase cell ring rotation during deployment. One goal here is to facilitate orientation of the rings after deployment and provide some scaffolding for tissue prolapse.

Alternatively, in some embodiments, one or more of the stent cells 14 (as illustrated in FIG. 25) or bends of an open stent pattern (not illustrated) can support substantially or completely closed loops or eyelets 412 having an opening 414 therein configured to receive a wire connector therethrough. The wire connector 402 can form double loops, lock knots, or other suitable connections with the loops 412.

FIG. 26 is a plan view of a portion of another embodiment of a stent 450 having a connector 452 between at least two adjacent stent segments 12 of a stent. The connector 452 can have a generally helical shape, comprising one or more loops. In some embodiments, the connector 452 can have two or more loops.

Additionally, in some embodiments, as in the illustrated embodiment, the connector 452 can have endpoints 454 that are circumferentially offset from one another so as to not be aligned longitudinally. In particular, the connector 452 can have a first endpoint 454a that is attached to stent cell 14a, and a second endpoint 454b that is attached to stent cell 14b. The endpoints 454 can be circumferentially offset by one or more cells 14. In some embodiments, as in the illustrated embodiment, the endpoints 454a, 454b can be circumferentially offset by two or more cells 14. In other embodiments (not illustrated), the endpoints 454 can be approximately longitudinally aligned when the stent 400 is in a collapsed state, an expanded state, or otherwise.

In some embodiments, a diameter of the connector 452 (as represented by D1 in FIG. 26) in the expanded state of the stent 450, can be approximately the same as, or slightly larger than, the relaxed inside diameter of the target vessel or passageway to provide additional scaffolding to the vessel. In some embodiments, the diameter D1 of the connector 452 in the expanded state of the stent 450 can be approximately as large as the size of three expanded cells 14.

Some embodiments of the stents disclosed herein can be configured such that no longitudinal connectors are positioned between two or more of the adjacent stent segments in a stent. In some embodiments, the entire stent be configured such that no stent segments are interconnected with connectors. Further, any of the stents or stent segments disclosed herein can be covered with a graft material, such as without limitation ePTFE. In some embodiments, portions of the stents or stent segments can be sutured to the graft material.

Figure 35:
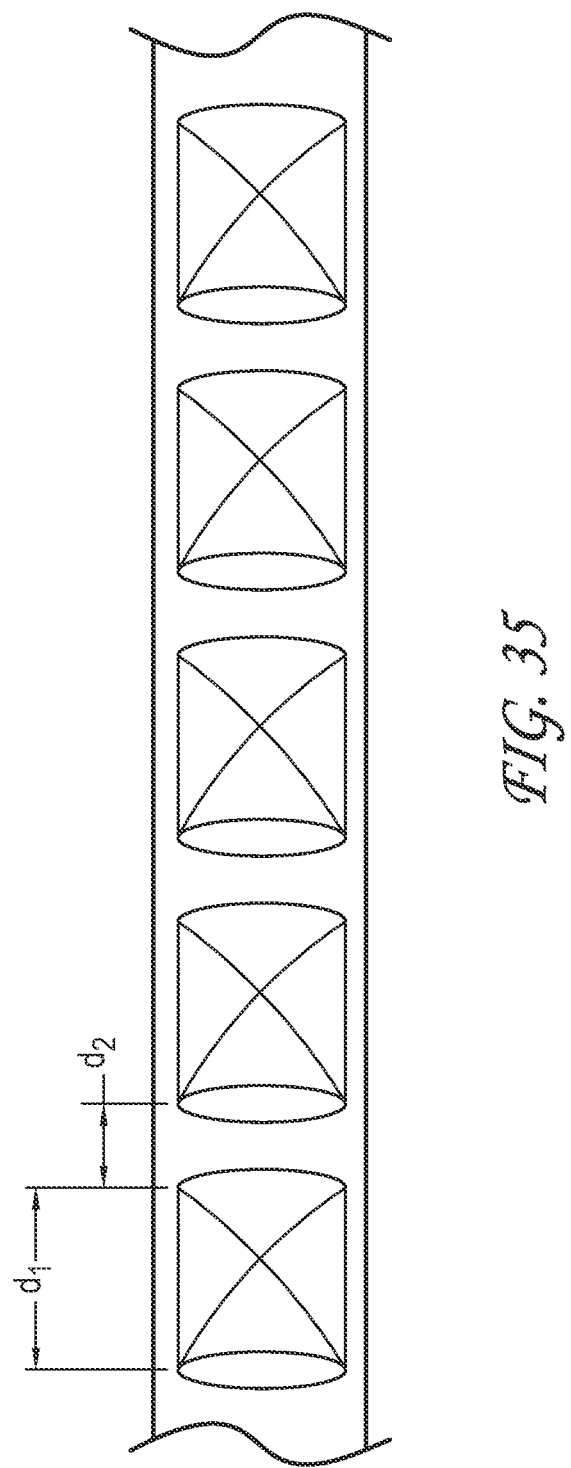

Further, in some embodiments, stent segments 12 (whether or not axial connectors are positioned between adjacent stent segments) can be deployed in a patient's vasculature or passageway such that a gap or space between adjacent stent segments (represented by d2 in FIG. 35) is approximately 15% of the axial length of one or more of the stent segments 12 (represented by d1 in FIG. 35), when the vessel or passageway is in a relaxed state. In some embodiments, stent segments 12 (whether or not axial connectors are positioned between adjacent stent segments) can be deployed in a patient's vasculature or passageway such that a gap or space between adjacent stent segments is from approximately 5% to approximately 50% of the axial length of one or more of the stent segments 12, or from approximately 15% to approximately 35% of the axial length of one or more of the stent segments 12, when the blood vessel or passageway is in a relaxed state.

Figure 35A:
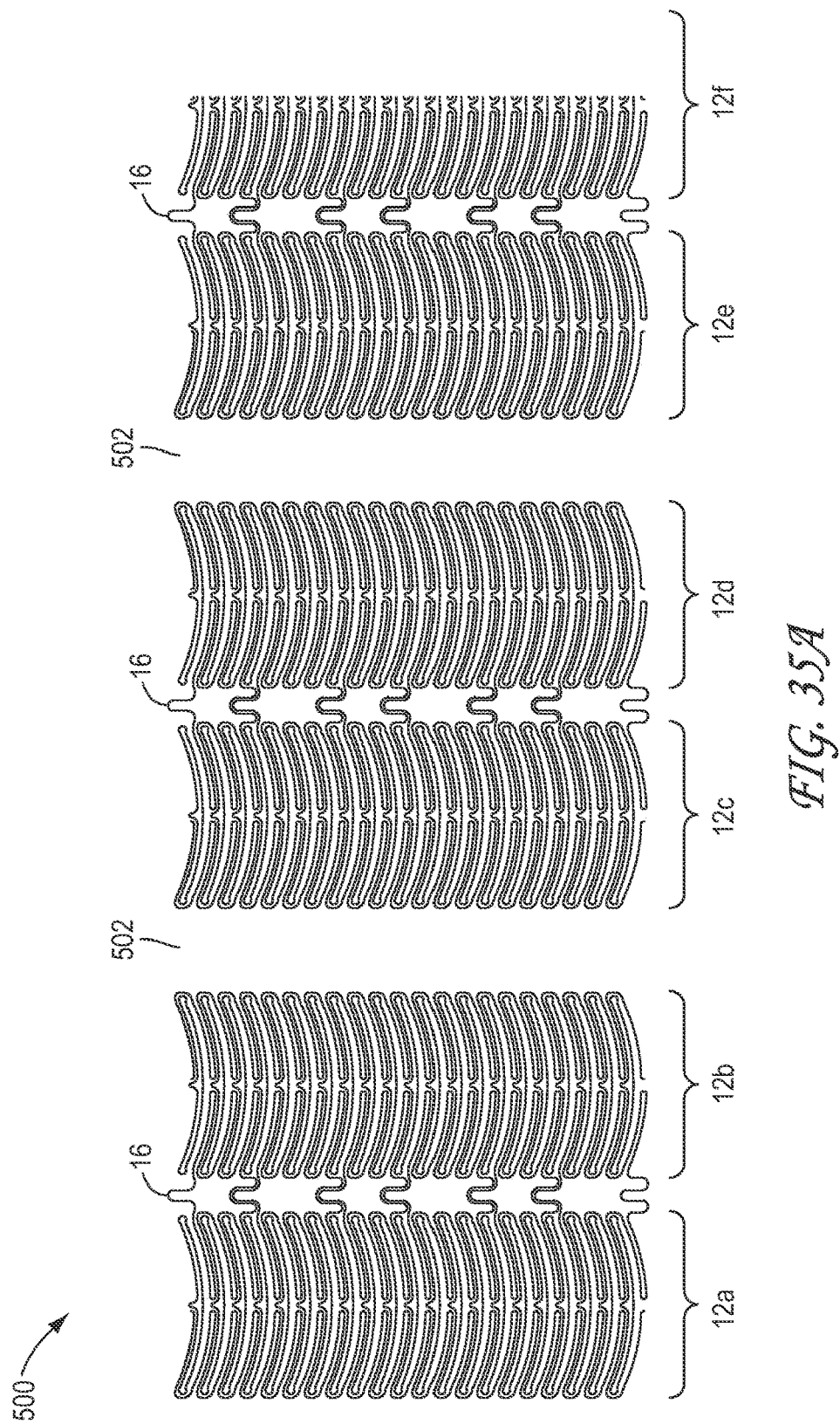
Figure 36:
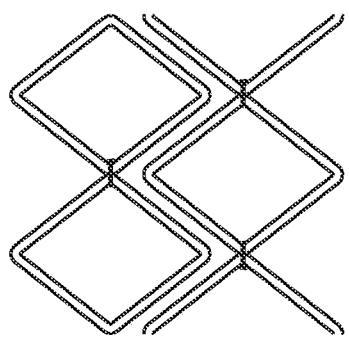
Figure 36:
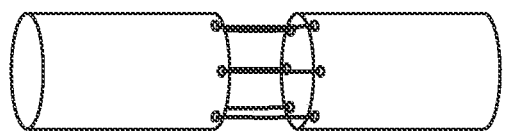
Figure 36:
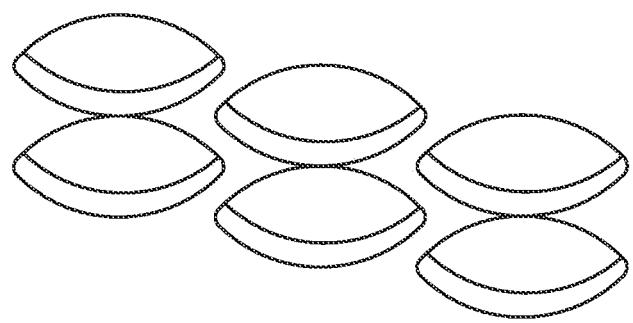
Figure 36:
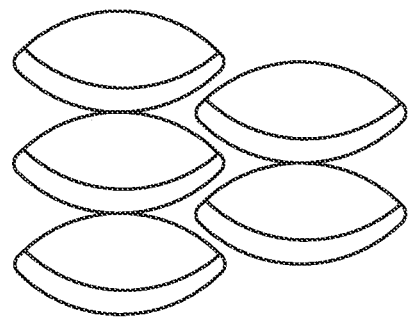
Figure 37:
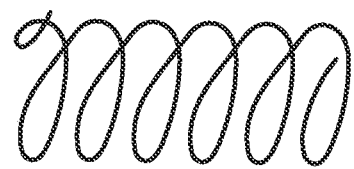
Figure 37:
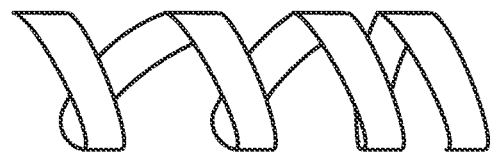
Figure 37:
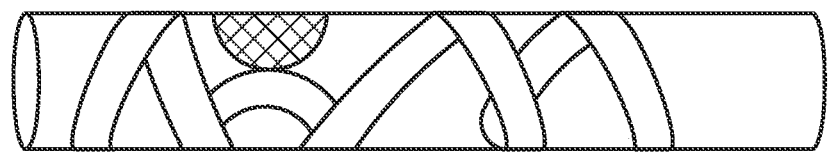

Additionally, some stent embodiments disclosed herein can have spaces or gaps between some of the adjacent stent segments, and connectors or sutures between other adjacent stent segments of the same stent. With reference to FIG. 35A, stent 500 is configured to have one or more connectors 16 between adjacent stent segments (or rings) 12a, 12b, between adjacent stent segments (or rings) 12c, 12d, and between adjacent stent segments (or rings) 12e, 12f. In some embodiments, severable connectors can be used in place of the connectors 16 shown in FIG. 35A. Further, the stent 500 can be configured such that there is a gap or space 502 between adjacent stent segments (or rings) 12b, 12c and between adjacent stent segments (or rings) 12d, 12e. Having connectors between pairs of adjacent stent segments 12 can increase the stability of the each of the interconnected stent segments of the pair by inhibiting each of the stent segments 12 of the pair from rolling, flipping, or otherwise rotating out of its proper orientation relative to the vessel lumen. Therefore, the connectors between each pair of stent segments 12 can be used to bias each ring of the pair to maintain an open orifice or passageway through the vessel. In some embodiments, all or any number of adjacent stent segments can have a gap or space therebetween.

FIGS. 27-37 set forth additional details regarding some embodiments of the stents and connectors disclosed herein.

Although the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It can be also contemplated that various combinations or subcombinations of the specific features and aspects of the embodiments may be made and still fall within the scope of the inventions. For example, in some embodiments, the features, configurations, or other details disclosed or incorporated by reference herein with respect to some of the connector or stent embodiments are combinable with other features, configurations, or details disclosed herein with respect to other connector or stent embodiments to form new embodiments not explicitly disclosed herein. All of such embodiments having combinations of features and configurations are contemplated as being part of this disclosure. Additionally, unless otherwise stated, no features or details of any of the stent or connector embodiments disclosed herein are meant to be required or essential to any of the embodiments disclosed herein, unless explicitly described herein as being required or essential.

Additionally, the connector embodiments disclosed herein can be used to interconnect any suitable stent structures, and can be configured to attach to or be supported by any suitable portion of the stent segments, stent cells, or other stent structures. For example, some embodiments of the connectors can be configured to be connectable to the apex of a stent cell, a portion of the stent cell adjacent to the apex, to the struts of the stent cells, or otherwise. Breakable inter-connect configurations can be on or off apex, valley to valley, valley to apex in various open and closed cell designs.

Accordingly, it should be understood that various features and aspects of the disclosed embodiments can be combined with or substituted for one another in order to form varying modes of the disclosed inventions. Thus, it can be intended that the scope of the present inventions herein disclosed should not be limited by the particular disclosed embodiments described above.

What is claimed is:

1. An expandable medical device for treating an endolumenal passageway, comprising:
   a first circumferential support structure having one or more closed cells;
   a second circumferential support structure having one or more closed cells, the second circumferential support structure being proximal of the first circumferential support structure; and
   an interconnect having a proximal end passing through one or more closed cells of the second circumferential support structure, a distal end passing through one or more closed cells of the first circumferential support structure, and an elongate portion extending between the proximal and distal ends,
   the interconnect having a first state providing a continuous material between the proximal and distal ends of the interconnect thereby engaging the first and second circumferential support structures,
   the interconnect having a second state in which a gap is provided therealong thereby disengaging the first and second circumferential support structures;
   wherein the interconnect enters the second state when the expandable device experiences a predetermined axial force or foreshortening.

2. The expandable device of claim 1, wherein the interconnect comprises a wire connector.

3. The expandable device of claim 2, wherein the wire connector comprises a thread structure that is collapsible in compression to facilitate foreshortening of the expandable device.

4. The expandable device of claim 2, wherein the wire connector comprises a material that biodegrades when in contact with human blood.

5. The expandable device of claim 2, wherein the wire connector comprises a helical strand having at least one turn disposed between the first and second circumferential support structures.

6. The expandable device of claim 2, wherein the wire connector is a metal alloy.

7. The expandable device of claim 1, wherein the interconnect is made of the same material as the first and second circumferential support structures.

8. The expandable device of claim 1, wherein the first and second circumferential support structures comprise closed cells extending entirely around a central axis of the expandable device.

9. The expandable device of claim 1, wherein the one or more closed cells of the first circumferential support structure or the second circumferential support structure are chosen from bistable cells, multistable cells, deformable unit cells, self-expandable cells, balloon expandable cells, and mechanically expandable cells.

10. The expandable device of claim 1, wherein the interconnect keeps the first and second circumferential support structures oriented so that an apex of each cell alternates with an apex of another cell.

11. The expandable device of claim 1, wherein the interconnect comprises a metal alloy.

12. An expandable medical device for treating an endolumenal passageway that is subject to axial foreshortening, comprising:
   a first circumferential support structure;
   a second circumferential support structure, the second circumferential support structure being proximal of the first circumferential support structure; and
   a moveable interconnect having a first portion connected to the first circumferential support structure and a second portion connected to the second circumferential support structure, the first and second portions of the moveable interconnect configured to be slidably coupled to one another,
   wherein the first portion includes a continuous piece of material that defines a longitudinal opening within the continuous piece of material and having a first end portion and a second end portion,
   wherein the second portion of the moveable interconnect comprises a tab positioned at a distal portion of the second portion,
   wherein the first portion is defined by a tubular shape having the longitudinal opening.

13. The expandable device of claim 12, wherein the tab has a size larger than a width of the longitudinal opening.

14. The expandable device of claim 12, wherein the tab can face radially outward or radially inward.

15. The expandable device of claim 12, wherein at least one of the first portion and the second portion comprises detents or channels that limit the range of translation of the second portion relative to the first portion.

16. The expandable device of claim 12, wherein the interconnect is positioned at an apex of a cell.

17. The expandable device of claim 12, wherein the interconnect is positioned off-center from an apex of a cell of the first circumferential support structure or the second circumferential support structure.

* * * * *